(12) United States Patent
Gopalakrishnan et al.

(10) Patent No.: US 10,159,415 B2
(45) Date of Patent: *Dec. 25, 2018

(54) METHODS AND SYSTEMS FOR ARRHYTHMIA TRACKING AND SCORING

(71) Applicant: AliveCor, Inc., San Francisco, CA (US)

(72) Inventors: Ravi Gopalakrishnan, San Francisco, CA (US); Lev Korzinov, San Francisco, CA (US); Fei Wang, San Francisco, CA (US); Euan Thomson, San Francisco, CA (US); Nupur Srivastava, San Francisco, CA (US); Omar Dawood, San Francisco, CA (US); Iman Abuzeid, San Francisco, CA (US); David E. Albert, San Francisco, CA (US)

(73) Assignee: ALIVECOR, INC., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/393,077

(22) Filed: Dec. 28, 2016

(65) Prior Publication Data

US 2017/0238814 A1    Aug. 24, 2017

Related U.S. Application Data

(63) Continuation of application No. 14/730,122, filed on Jun. 3, 2015, now Pat. No. 9,572,499, which is a (Continued)

(51) Int. Cl.
*A61B 5/04* (2006.01)
*A61B 5/0205* (2006.01)
(Continued)

(52) U.S. Cl.
CPC ........ *A61B 5/02055* (2013.01); *A61B 5/0022* (2013.01); *A61B 5/0245* (2013.01); (Continued)

(58) Field of Classification Search
USPC .................................................. 600/508–509
See application file for complete search history.

(56) References Cited

U.S. PATENT DOCUMENTS

| 3,717,857 A | 2/1973 | Evans |
| 3,731,311 A | 5/1973 | Williams |

(Continued)

FOREIGN PATENT DOCUMENTS

| CH | 675675 A5 | 10/1990 |
| CN | 1798522 A | 7/2006 |

(Continued)

OTHER PUBLICATIONS

Adidas miCoach Pacer Review: Like Nike+, Only Better; printed from website http://gizmodo.com/5479456/adidas• printed on Mar. 4, 2010. 5 pages.

(Continued)

*Primary Examiner* — Nicole F Johnson
(74) *Attorney, Agent, or Firm* — Womble Bond Dickinson (US) LLP; Christopher Kokoska

(57) ABSTRACT

A dashboard centered around arrhythmia or atrial fibrillation tracking is provided. The dashboard includes a heart or cardiac health score that can be calculated in response to data from the user such as their ECG and other personal information and cardiac health influencing factors. The dashboard also provides to the user recommendations or goals, such as daily goals, for the user to meet and thereby improve their heart or cardiac health score. These goals and recommendations may be set by the user or a medical professional and routinely updated as his or her heart or cardiac health score improves or otherwise changes. The dashboard is generally displayed from an application provided on a smartphone or tablet computer of the user.

20 Claims, 16 Drawing Sheets

Related U.S. Application Data continuation of application No. 14/569,513, filed on Dec. 12, 2014, now Pat. No. 9,420,956.

(60) Provisional application No. 61/915,113, filed on Dec. 12, 2013, provisional application No. 61/953,616, filed on Mar. 14, 2014, provisional application No. 61/969,019, filed on Mar. 21, 2014, provisional application No. 61/970,551, filed on Mar. 26, 2014, provisional application No. 62/014,516, filed on Jun. 19, 2014.

(51) Int. Cl.
| | | |
|---|---|---|
| *A61B 5/024* | (2006.01) | |
| *A61B 5/0245* | (2006.01) | |
| *A61B 5/046* | (2006.01) | |
| *A61B 5/00* | (2006.01) | |
| *G06F 19/00* | (2018.01) | |
| *G16H 15/00* | (2018.01) | |
| *G16H 10/60* | (2018.01) | |
| *A61B 5/021* | (2006.01) | |
| *A61B 5/0452* | (2006.01) | |
| *A61B 5/11* | (2006.01) | |
| *G16H 50/30* | (2018.01) | |

(52) U.S. Cl.
CPC ...... *A61B 5/02405* (2013.01); *A61B 5/02416* (2013.01); *A61B 5/046* (2013.01); *A61B 5/681* (2013.01); *A61B 5/6898* (2013.01); *A61B 5/7264* (2013.01); *A61B 5/7275* (2013.01); *A61B 5/746* (2013.01); *G06F 19/00* (2013.01); *G06F 19/3418* (2013.01); *A61B 5/021* (2013.01); *A61B 5/02438* (2013.01); *A61B 5/0452* (2013.01); *A61B 5/1118* (2013.01); *G06F 19/3481* (2013.01); *G16H 10/60* (2018.01); *G16H 15/00* (2018.01); *G16H 50/30* (2018.01)

(56) References Cited

U.S. PATENT DOCUMENTS

| | | |
|---|---|---|
| 3,768,014 A | 10/1973 | Smith et al. |
| 3,776,228 A | 12/1973 | Semler |
| 3,779,237 A | 12/1973 | Roth et al. |
| 3,779,249 A | 12/1973 | Semler |
| 3,782,367 A | 1/1974 | Hochberg et al. |
| 3,805,227 A | 4/1974 | Lester |
| 3,882,277 A | 5/1975 | Depedro et al. |
| 3,885,552 A | 5/1975 | Kennedy |
| 3,898,984 A | 8/1975 | Mandel et al. |
| 3,909,599 A | 9/1975 | Trott, Jr. et al. |
| 4,027,146 A | 5/1977 | Gilmore |
| 4,045,767 A | 8/1977 | Nishihara et al. |
| 4,083,366 A | 4/1978 | Gombrich et al. |
| 4,095,050 A | 6/1978 | Beachem et al. |
| 4,221,223 A | 9/1980 | Linden |
| 4,230,127 A | 10/1980 | Larson |
| 4,231,031 A | 10/1980 | Crowther et al. |
| 4,250,888 A | 2/1981 | Grosskopf |
| 4,281,664 A | 8/1981 | Duggan |
| 4,295,472 A | 10/1981 | Adams |
| 4,312,358 A | 1/1982 | Barney |
| 4,318,130 A | 3/1982 | Heuer |
| 4,364,397 A | 12/1982 | Citron et al. |
| 4,367,752 A | 1/1983 | Jimenez et al. |
| 4,409,984 A | 10/1983 | Dick |
| 4,531,527 A | 7/1985 | Reinhold, Jr. et al. |
| 4,567,883 A | 2/1986 | Langer et al. |
| 4,572,182 A | 2/1986 | Royse |
| 4,580,250 A | 4/1986 | Kago et al. |
| 4,583,553 A | 4/1986 | Shah et al. |
| 4,622,979 A | 11/1986 | Katchis et al. |
| 4,625,730 A | 12/1986 | Fountain et al. |
| 4,803,625 A | 2/1989 | Fu et al. |
| 4,889,131 A | 12/1989 | Salem et al. |
| 4,920,489 A | 4/1990 | Hubelbank et al. |
| 4,938,228 A | 7/1990 | Righter et al. |
| 4,938,229 A | 7/1990 | Bergelson et al. |
| 4,958,641 A | 9/1990 | Digby et al. |
| 4,977,899 A | 12/1990 | Digby et al. |
| 4,981,141 A | 1/1991 | Segalowitz |
| 5,012,814 A | 5/1991 | Mills et al. |
| 5,023,906 A | 6/1991 | Novas |
| 5,025,794 A | 6/1991 | Albert et al. |
| 5,058,597 A | 10/1991 | Onoda et al. |
| 5,090,418 A | 2/1992 | Squires et al. |
| 5,111,396 A | 5/1992 | Mills et al. |
| 5,128,552 A | 7/1992 | Fang et al. |
| 5,136,555 A | 8/1992 | Gardos |
| 5,181,552 A | 1/1993 | Eiermann |
| 5,191,891 A | 3/1993 | Righter |
| 5,201,321 A | 4/1993 | Fulton |
| 5,218,969 A | 6/1993 | Bredesen et al. |
| 5,226,424 A | 7/1993 | Bible |
| 5,238,001 A | 8/1993 | Gallant et al. |
| D341,659 S | 11/1993 | Homayoun et al. |
| 5,259,387 A | 11/1993 | Depinto |
| 5,301,679 A | 4/1994 | Taylor |
| 5,304,186 A | 4/1994 | Semler et al. |
| 5,313,953 A | 5/1994 | Yomtov et al. |
| 5,321,618 A | 6/1994 | Gessman |
| 5,333,616 A | 8/1994 | Mills et al. |
| 5,336,245 A | 8/1994 | Adams et al. |
| 5,337,752 A | 8/1994 | Reeves |
| 5,339,824 A | 8/1994 | Engira |
| 5,343,869 A | 9/1994 | Pross et al. |
| 5,343,870 A | 9/1994 | Gallant et al. |
| 5,348,008 A | 9/1994 | Bornn et al. |
| 5,360,005 A | 11/1994 | Wilk |
| 5,365,935 A | 11/1994 | Righter et al. |
| 5,410,587 A | 4/1995 | Grunwell |
| 5,417,222 A | 5/1995 | Dempsey et al. |
| 5,433,736 A | 7/1995 | Nilsson |
| 5,452,356 A | 9/1995 | Albert |
| 5,466,246 A | 11/1995 | Silvian |
| 5,467,773 A | 11/1995 | Bergelson et al. |
| 5,481,255 A | 1/1996 | Albert et al. |
| 5,503,158 A | 4/1996 | Coppock et al. |
| 5,518,001 A | 5/1996 | Snell |
| 5,522,396 A | 6/1996 | Langer et al. |
| 5,539,705 A | 7/1996 | Akerman et al. |
| D372,785 S | 8/1996 | Sabri |
| 5,544,661 A | 8/1996 | Davis et al. |
| 5,551,953 A | 9/1996 | Lattin et al. |
| 5,561,712 A | 10/1996 | Nishihara |
| 5,568,448 A | 10/1996 | Tanigushi et al. |
| 5,579,284 A | 11/1996 | May |
| D377,983 S | 2/1997 | Sabri et al. |
| 5,608,723 A | 3/1997 | Felsenstein |
| 5,634,468 A | 6/1997 | Platt et al. |
| 5,652,570 A | 7/1997 | Lepkofker |
| 5,661,699 A | 8/1997 | Sutton |
| 5,675,325 A | 10/1997 | Taniguchi et al. |
| 5,678,562 A | 10/1997 | Sellers |
| 5,701,894 A | 12/1997 | Cherry et al. |
| 5,704,364 A | 1/1998 | Saltzstein et al. |
| 5,724,025 A | 3/1998 | Tavori |
| 5,730,143 A | 3/1998 | Schwarzberg |
| 5,735,285 A | 4/1998 | Albert et al. |
| 5,742,251 A | 4/1998 | Gerber |
| 5,748,103 A | 5/1998 | Flach et al. |
| 5,764,763 A | 6/1998 | Jensen et al. |
| 5,772,586 A | 6/1998 | Heinonen et al. |
| 5,818,788 A | 10/1998 | Kimura et al. |
| 5,825,718 A | 10/1998 | Ueki et al. |
| 5,827,179 A | 10/1998 | Lichter et al. |
| 5,840,020 A | 11/1998 | Heinonen et al. |
| 5,844,997 A | 12/1998 | Murphy, Jr. |
| 5,861,018 A | 1/1999 | Feierbach |
| 5,873,369 A | 2/1999 | Laniado et al. |

(56) References Cited

U.S. PATENT DOCUMENTS

| | | |
|---|---|---|
| 5,876,351 A | 3/1999 | Rohde |
| 5,877,675 A | 3/1999 | Rebstock et al. |
| 5,889,730 A | 3/1999 | May |
| 5,929,761 A | 7/1999 | Van Der Laan et al. |
| D414,870 S | 10/1999 | Saltzstein et al. |
| 5,970,388 A | 10/1999 | Will |
| 5,976,083 A | 11/1999 | Richardson et al. |
| 5,982,297 A | 11/1999 | Welle |
| 5,983,127 A | 11/1999 | Depinto |
| 6,008,703 A | 12/1999 | Perrott et al. |
| 6,024,705 A | 2/2000 | Schlager et al. |
| 6,037,704 A | 3/2000 | Welle |
| 6,047,206 A | 4/2000 | Albrecht et al. |
| 6,047,257 A | 4/2000 | Dewaele |
| 6,048,319 A | 4/2000 | Hudgins et al. |
| D427,315 S | 6/2000 | Saltzstein et al. |
| 6,072,396 A | 6/2000 | Gaukel |
| 6,083,248 A | 7/2000 | Thompson |
| 6,084,510 A | 7/2000 | Lemelson et al. |
| 6,102,856 A | 8/2000 | Groff et al. |
| 6,153,532 A | 11/2000 | Dow et al. |
| 6,159,147 A | 12/2000 | Lichter et al. |
| 6,198,394 B1 | 3/2001 | Jacobsen et al. |
| 6,224,548 B1 | 5/2001 | Gopinathan et al. |
| 6,236,889 B1 | 5/2001 | Soykan et al. |
| 6,264,614 B1 | 7/2001 | Albert et al. |
| 6,282,440 B1 | 8/2001 | Brodnick et al. |
| 6,282,441 B1 | 8/2001 | Raymond et al. |
| 6,289,238 B1 | 9/2001 | Besson et al. |
| 6,319,201 B1 | 11/2001 | Wilk |
| 6,343,049 B1 | 1/2002 | Toda |
| 6,363,139 B1 | 3/2002 | Zurek et al. |
| 6,364,834 B1 | 4/2002 | Reuss et al. |
| 6,366,871 B1 | 4/2002 | Geva |
| 6,377,843 B1 | 4/2002 | Naydenov et al. |
| 6,418,394 B1 | 7/2002 | Puolakanaho et al. |
| 6,433,689 B1 | 8/2002 | Hovind et al. |
| 6,453,164 B1 | 9/2002 | Fuller et al. |
| 6,478,736 B1 | 11/2002 | Mault |
| 6,485,416 B1 | 11/2002 | Platt et al. |
| 6,507,734 B1 | 1/2003 | Berger et al. |
| 6,513,532 B2 | 2/2003 | Mault et al. |
| 6,549,756 B1 | 4/2003 | Engstrom |
| 6,558,320 B1 | 5/2003 | Causey, III et al. |
| 6,579,231 B1 | 6/2003 | Phipps |
| 6,595,929 B2 | 7/2003 | Stivoric et al. |
| 6,600,471 B2 | 7/2003 | Lee et al. |
| 6,605,038 B1 | 8/2003 | Teller et al. |
| 6,612,985 B2 | 9/2003 | Eiffert et al. |
| 6,616,613 B1 | 9/2003 | Goodman |
| 6,636,761 B2 | 10/2003 | Brodnick |
| 6,685,633 B2 | 2/2004 | Albert et al. |
| 6,717,983 B1 | 4/2004 | Toda |
| 6,790,178 B1 | 9/2004 | Mault et al. |
| 6,804,558 B2 | 10/2004 | Haller et al. |
| 6,820,057 B1 | 11/2004 | Loch et al. |
| 6,845,263 B2 | 1/2005 | Kawaguchi |
| 6,893,396 B2 | 5/2005 | Schulze et al. |
| 6,928,535 B2 | 8/2005 | Yamashita et al. |
| 6,950,681 B2 | 9/2005 | Hofmann |
| 6,970,737 B1 | 11/2005 | Brodnick et al. |
| 6,987,965 B2 | 1/2006 | Ng et al. |
| 7,018,339 B2 | 3/2006 | Birnbaum et al. |
| 7,020,508 B2 | 3/2006 | Stivoric et al. |
| 7,031,745 B2 | 4/2006 | Shen |
| 7,061,381 B2 | 6/2006 | Forcier et al. |
| 7,103,407 B2 | 9/2006 | Hjelt et al. |
| 7,107,095 B2 | 9/2006 | Manolas |
| 7,108,659 B2 | 9/2006 | Ross et al. |
| 7,153,262 B2 | 12/2006 | Stivoric et al. |
| 7,162,291 B1 | 1/2007 | Nachaliel |
| 7,162,294 B2 | 1/2007 | Rowlandson et al. |
| 7,188,151 B2 | 3/2007 | Kumar et al. |
| 7,222,054 B2 | 5/2007 | Geva |
| 7,236,818 B2 | 6/2007 | McLeod et al. |
| 7,257,448 B2 | 8/2007 | Crowe et al. |
| 7,260,429 B2 | 8/2007 | Siejko et al. |
| 7,261,690 B2 | 8/2007 | Teller et al. |
| 7,285,090 B2 | 10/2007 | Stivoric et al. |
| 7,319,425 B2 | 1/2008 | Fiorenza et al. |
| 7,324,836 B2 | 1/2008 | Steenstra et al. |
| 7,349,574 B1 | 3/2008 | Sodini et al. |
| 7,351,207 B2 | 4/2008 | Priemer |
| 7,354,400 B2 | 4/2008 | Asafusa et al. |
| 7,382,247 B2 | 6/2008 | Welch et al. |
| 7,383,297 B1 | 6/2008 | Atsmon et al. |
| 7,398,115 B2 | 7/2008 | Lynn |
| 7,415,304 B2 | 8/2008 | Rowlandson et al. |
| 7,444,116 B2 | 10/2008 | Ivanov et al. |
| 7,460,899 B2 | 12/2008 | Almen |
| 7,502,643 B2 | 3/2009 | Farringdon et al. |
| 7,509,159 B2 | 3/2009 | Xue et al. |
| 7,515,043 B2 | 4/2009 | Welch et al. |
| 7,515,044 B2 | 4/2009 | Welch et al. |
| 7,520,860 B2 | 4/2009 | Guion-Johnson et al. |
| 7,542,878 B2 | 6/2009 | Nanikashvili |
| 7,548,623 B2 | 6/2009 | Manabe |
| 7,596,405 B2 | 9/2009 | Kurzweil et al. |
| 7,603,148 B2 | 10/2009 | Michalak |
| 7,647,185 B2 | 1/2010 | Tarassenko et al. |
| 7,654,148 B2 | 2/2010 | Tomlinson et al. |
| 7,657,479 B2 | 2/2010 | Henley |
| 7,668,589 B2 | 2/2010 | Bauer |
| 7,689,437 B1 | 3/2010 | Teller et al. |
| 7,701,895 B2 | 4/2010 | Gehasie et al. |
| 7,733,224 B2 | 6/2010 | Tran |
| 7,742,808 B2 | 6/2010 | Nissila et al. |
| 7,806,832 B2 | 10/2010 | Gallagher et al. |
| 7,819,814 B2 | 10/2010 | Gavriely et al. |
| 7,846,104 B2 | 12/2010 | MacQuarrie et al. |
| 7,846,106 B2 | 12/2010 | Andrews et al. |
| 7,904,160 B2 | 3/2011 | Brodnick et al. |
| 7,945,064 B2 | 5/2011 | O'Brien et al. |
| 7,946,959 B2 | 5/2011 | Shum et al. |
| 7,955,273 B2 | 6/2011 | Rahe-Meyer |
| 7,983,749 B2 | 7/2011 | Warren |
| 8,019,609 B2 | 9/2011 | Tamir et al. |
| 8,034,006 B2 | 10/2011 | Celik-Butler et al. |
| 8,062,090 B2 | 11/2011 | Atsmon et al. |
| 8,078,136 B2 | 12/2011 | Atsmon et al. |
| 8,078,278 B2 | 12/2011 | Penner |
| 8,126,526 B2 | 2/2012 | Kitajima et al. |
| 8,126,566 B2 | 2/2012 | Stahmann et al. |
| 8,126,728 B2 | 2/2012 | Dicks et al. |
| 8,130,093 B2 | 3/2012 | Mazar et al. |
| 8,150,750 B2 | 4/2012 | Ray |
| 8,160,276 B2 | 4/2012 | Liao et al. |
| 8,165,677 B2 | 4/2012 | Von et al. |
| 8,216,136 B2 | 7/2012 | Addison et al. |
| 8,224,429 B2 | 7/2012 | Prstojevich et al. |
| 8,265,907 B2 | 9/2012 | Nanikashvili et al. |
| 8,275,553 B2 | 9/2012 | Ochs et al. |
| 8,275,635 B2 | 9/2012 | Stivoric et al. |
| 8,282,550 B2 | 10/2012 | Rasdal et al. |
| 8,285,356 B2 | 10/2012 | Bly et al. |
| 8,301,232 B2 | 10/2012 | Albert et al. |
| 8,301,236 B2 | 10/2012 | Baumann et al. |
| 8,323,188 B2 | 12/2012 | Tran |
| 8,328,718 B2 | 12/2012 | Tran |
| 8,332,233 B2 | 12/2012 | Ott et al. |
| 8,364,250 B2 | 1/2013 | Moon et al. |
| 8,369,936 B2 | 2/2013 | Farringdon et al. |
| 8,374,688 B2 | 2/2013 | Libbus et al. |
| 8,449,471 B2 | 5/2013 | Tran |
| 8,500,636 B2 | 8/2013 | Tran |
| 8,509,882 B2 | 8/2013 | Albert et al. |
| 8,519,835 B2 | 8/2013 | Dunko |
| 8,543,185 B2 | 9/2013 | Yuen et al. |
| 8,548,577 B2 | 10/2013 | Muhlsteff et al. |
| 8,548,770 B2 | 10/2013 | Yuen et al. |
| 8,700,137 B2 | 4/2014 | Albert |
| 8,725,229 B2 | 5/2014 | Furue et al. |
| 8,755,871 B2 | 6/2014 | Weng et al. |
| 8,823,490 B2 | 9/2014 | Libbus et al. |

(56) References Cited

U.S. PATENT DOCUMENTS

| | | |
|---|---|---|
| 8,923,958 B2 | 12/2014 | Gupta et al. |
| 8,951,189 B2 | 2/2015 | Osorio |
| 8,951,192 B2 | 2/2015 | Osorio |
| 8,974,396 B1 | 3/2015 | Brady et al. |
| 8,977,347 B2 | 3/2015 | Mestha et al. |
| 9,026,202 B2 | 5/2015 | Albert |
| 9,220,430 B2 | 12/2015 | Albert |
| 9,254,095 B2 | 2/2016 | Galloway et al. |
| 9,351,654 B2 | 5/2016 | Albert |
| 9,420,956 B2 | 8/2016 | Gopalakrishnan et al. |
| 9,572,499 B2 | 2/2017 | Gopalakrishnan et al. |
| 2001/0027384 A1 | 10/2001 | Schulze et al. |
| 2001/0031998 A1 | 10/2001 | Nelson et al. |
| 2001/0051766 A1 | 12/2001 | Gazdzinski |
| 2002/0016541 A1 | 2/2002 | Glossop |
| 2002/0032386 A1 | 3/2002 | Sackner et al. |
| 2002/0111556 A1 | 8/2002 | Wegner |
| 2002/0143576 A1 | 10/2002 | Nolvak et al. |
| 2003/0004425 A1 | 1/2003 | Narimatsu et al. |
| 2003/0093002 A1 | 5/2003 | Kuo |
| 2003/0107487 A1 | 6/2003 | Korman et al. |
| 2003/0117987 A1 | 6/2003 | Brebner |
| 2003/0149344 A1 | 8/2003 | Nizan |
| 2003/0193839 A1 | 10/2003 | Singh |
| 2004/0034284 A1 | 2/2004 | Aversano et al. |
| 2004/0044292 A1 | 3/2004 | Yasushi et al. |
| 2004/0059205 A1 | 3/2004 | Carlson et al. |
| 2004/0117212 A1 | 6/2004 | Kong et al. |
| 2004/0120356 A1 | 6/2004 | Davenport et al. |
| 2004/0143403 A1 | 7/2004 | Brandon et al. |
| 2004/0215088 A1 | 10/2004 | Hubelbank |
| 2004/0215094 A1 | 10/2004 | Baumer et al. |
| 2004/0220487 A1 | 11/2004 | Vyshedskiy et al. |
| 2004/0220488 A1 | 11/2004 | Vyshedskiy et al. |
| 2004/0225199 A1 | 11/2004 | Evanyk et al. |
| 2004/0228217 A1 | 11/2004 | Szeto |
| 2004/0236819 A1 | 11/2004 | Anati et al. |
| 2004/0266407 A1 | 12/2004 | Lee et al. |
| 2004/0266480 A1 | 12/2004 | Hjelt et al. |
| 2005/0014531 A1 | 1/2005 | Findikli |
| 2005/0027207 A1 | 2/2005 | Westbrook et al. |
| 2005/0078533 A1 | 4/2005 | Vyshedskiy et al. |
| 2005/0124864 A1 | 6/2005 | Mack et al. |
| 2005/0234353 A1 | 10/2005 | Xue et al. |
| 2005/0239493 A1 | 10/2005 | Batkin et al. |
| 2006/0022833 A1 | 2/2006 | Ferguson et al. |
| 2006/0047215 A1 | 3/2006 | Newman et al. |
| 2006/0173259 A1 | 8/2006 | Flaherty et al. |
| 2006/0190045 A1 | 8/2006 | Marcus et al. |
| 2006/0193270 A1 | 8/2006 | Gehasie et al. |
| 2006/0252999 A1 | 11/2006 | Devaul et al. |
| 2007/0021677 A1 | 1/2007 | Markel |
| 2007/0027386 A1 | 2/2007 | Such et al. |
| 2007/0032731 A1 | 2/2007 | Lovejoy et al. |
| 2007/0063850 A1 | 3/2007 | Devaul et al. |
| 2007/0073266 A1 | 3/2007 | Chmiel et al. |
| 2007/0106179 A1 | 5/2007 | Bagha et al. |
| 2007/0156060 A1 | 7/2007 | Cervantes et al. |
| 2007/0167850 A1 | 7/2007 | Russell et al. |
| 2007/0254604 A1 | 11/2007 | Kim |
| 2007/0265038 A1 | 11/2007 | Kim |
| 2008/0009759 A1 | 1/2008 | Chetham et al. |
| 2008/0058670 A1 | 3/2008 | Mainini |
| 2008/0112885 A1 | 5/2008 | Okunev et al. |
| 2008/0146890 A1 | 6/2008 | Leboeuf et al. |
| 2008/0146892 A1 | 6/2008 | Leboeuf et al. |
| 2008/0171945 A1 | 7/2008 | Dotter |
| 2008/0177162 A1 | 7/2008 | Bae et al. |
| 2008/0198872 A1 | 8/2008 | Pierce |
| 2008/0214903 A1 | 9/2008 | Orbach |
| 2008/0228045 A1 | 9/2008 | Gao et al. |
| 2008/0293453 A1 | 11/2008 | Atlas et al. |
| 2008/0300641 A1 | 12/2008 | Brunekreeft et al. |
| 2009/0010461 A1 | 1/2009 | Klinghult et al. |
| 2009/0024045 A1 | 1/2009 | Prakash et al. |
| 2009/0037575 A1 | 2/2009 | Crystal et al. |
| 2009/0069642 A1 | 3/2009 | Gao et al. |
| 2009/0117883 A1 | 5/2009 | Coffing et al. |
| 2009/0144080 A1 | 6/2009 | Gray et al. |
| 2009/0149767 A1 | 6/2009 | Rossetti |
| 2009/0156908 A1 | 6/2009 | Belalcazar et al. |
| 2009/0171170 A1 | 7/2009 | Li et al. |
| 2009/0209873 A1 | 8/2009 | Pinter et al. |
| 2009/0273467 A1 | 11/2009 | Elixmann et al. |
| 2009/0279389 A1 | 11/2009 | Irie |
| 2009/0287067 A1 | 11/2009 | Dorogusker et al. |
| 2009/0306485 A1 | 12/2009 | Bell |
| 2009/0312655 A1 | 12/2009 | Lo |
| 2010/0027379 A1 | 2/2010 | Saulnier et al. |
| 2010/0033303 A1 | 2/2010 | Dugan et al. |
| 2010/0035927 A1 | 2/2010 | Ojika et al. |
| 2010/0042008 A1 | 2/2010 | Amitai et al. |
| 2010/0049006 A1 | 2/2010 | Magar et al. |
| 2010/0049037 A1 | 2/2010 | Pinter et al. |
| 2010/0063381 A1 | 3/2010 | Greiser |
| 2010/0069735 A1 | 3/2010 | Berkner |
| 2010/0076276 A1 | 3/2010 | Gilland |
| 2010/0076331 A1 | 3/2010 | Chan et al. |
| 2010/0094152 A1 | 4/2010 | Semmlow |
| 2010/0113950 A1 | 5/2010 | Lin et al. |
| 2010/0148956 A1 | 6/2010 | Song et al. |
| 2010/0184479 A1 | 7/2010 | Griffin, Jr. |
| 2010/0185101 A1 | 7/2010 | Sakai et al. |
| 2010/0204758 A1 | 8/2010 | Boon et al. |
| 2010/0208434 A1 | 8/2010 | Kim et al. |
| 2010/0217099 A1 | 8/2010 | Leboeuf et al. |
| 2010/0217100 A1 | 8/2010 | Leboeuf et al. |
| 2010/0217345 A1 | 8/2010 | Wolfe et al. |
| 2010/0234746 A1 | 9/2010 | Sebelius et al. |
| 2010/0256509 A1 | 10/2010 | Kuo et al. |
| 2010/0256976 A1 | 10/2010 | Atsmon et al. |
| 2010/0281261 A1 | 11/2010 | Razzell |
| 2010/0298711 A1 | 11/2010 | Pedersen et al. |
| 2010/0324378 A1 | 12/2010 | Tran et al. |
| 2010/0331631 A1 | 12/2010 | MacLaughlin |
| 2011/0015496 A1 | 1/2011 | Sherman et al. |
| 2011/0035927 A1 | 2/2011 | Griffin et al. |
| 2011/0060251 A1 | 3/2011 | Verma et al. |
| 2011/0066042 A1 | 3/2011 | Pandia et al. |
| 2011/0117529 A1 | 5/2011 | Barash et al. |
| 2011/0134725 A1 | 6/2011 | Su et al. |
| 2011/0160601 A1 | 6/2011 | Wang et al. |
| 2011/0182445 A1 | 7/2011 | Atsmon et al. |
| 2011/0208076 A1 | 8/2011 | Fong et al. |
| 2011/0235466 A1 | 9/2011 | Booij et al. |
| 2011/0275950 A1 | 11/2011 | Xue et al. |
| 2011/0288425 A1 | 11/2011 | Stewart |
| 2011/0301435 A1 | 12/2011 | Albert et al. |
| 2011/0301439 A1 | 12/2011 | Albert et al. |
| 2012/0051187 A1 | 3/2012 | Paulson et al. |
| 2012/0053424 A1 | 3/2012 | Kenalty et al. |
| 2012/0071734 A1 | 3/2012 | Shimuta et al. |
| 2012/0083705 A1 | 4/2012 | Yuen et al. |
| 2012/0101396 A1 | 4/2012 | Solosko et al. |
| 2012/0108916 A1 | 5/2012 | Riftine |
| 2012/0123891 A1 | 5/2012 | Patel |
| 2012/0127833 A1 | 5/2012 | Ghen et al. |
| 2012/0143018 A1 | 6/2012 | Skidmore et al. |
| 2012/0147921 A1 | 6/2012 | Conti et al. |
| 2012/0157019 A1 | 6/2012 | Li |
| 2012/0158090 A1 | 6/2012 | Chavan et al. |
| 2012/0171963 A1 | 7/2012 | Tsfaty |
| 2012/0172689 A1 | 7/2012 | Albert et al. |
| 2012/0179056 A1 | 7/2012 | Moulder et al. |
| 2012/0197148 A1* | 8/2012 | Levitan .............. A61B 5/02405 600/515 |
| 2012/0285588 A1 | 11/2012 | Sheppard |
| 2012/0289790 A1 | 11/2012 | Jain et al. |
| 2012/0316413 A1 | 12/2012 | Liu et al. |
| 2013/0003852 A1 | 1/2013 | Yamamoto |
| 2013/0030259 A1 | 1/2013 | Thomsen et al. |
| 2013/0085364 A1 | 4/2013 | Lu et al. |
| 2013/0122810 A1 | 5/2013 | Kaufman |
| 2013/0156194 A1 | 6/2013 | Tanioka |

(56) References Cited

U.S. PATENT DOCUMENTS

| | | |
|---|---|---|
| 2013/0159699 A1 | 6/2013 | Torkkel |
| 2013/0197320 A1 | 8/2013 | Albert et al. |
| 2013/0236980 A1 | 9/2013 | Moretti et al. |
| 2013/0261414 A1 | 10/2013 | Tal et al. |
| 2013/0281816 A1 | 10/2013 | Strauss et al. |
| 2013/0289366 A1 | 10/2013 | Chua et al. |
| 2013/0331663 A1 | 12/2013 | Albert et al. |
| 2014/0050321 A1 | 2/2014 | Albert et al. |
| 2014/0051941 A1 | 2/2014 | Messerschmidt |
| 2014/0051946 A1 | 2/2014 | Arne et al. |
| 2014/0066798 A1 | 3/2014 | Albert |
| 2014/0073486 A1 | 3/2014 | Ahmed et al. |
| 2014/0073969 A1 | 3/2014 | Zou et al. |
| 2014/0094707 A1 | 4/2014 | Farringdon et al. |
| 2014/0114166 A1 | 4/2014 | Baxi |
| 2014/0163927 A1 | 6/2014 | Molettiere et al. |
| 2014/0221859 A1 | 8/2014 | Albert |
| 2014/0276162 A1 | 9/2014 | Albert et al. |
| 2015/0018660 A1 | 1/2015 | Thomson et al. |
| 2015/0073285 A1 | 3/2015 | Albert et al. |
| 2015/0087952 A1 | 3/2015 | David et al. |
| 2015/0182132 A1 | 7/2015 | Harris et al. |
| 2015/0265164 A1 | 9/2015 | Gopalakrishnan et al. |
| 2015/0297134 A1 | 10/2015 | Albert et al. |
| 2016/0071392 A1 | 3/2016 | Hankey et al. |
| 2016/0235319 A1 | 8/2016 | Albert |
| 2016/0331247 A1 | 11/2016 | Albert |

FOREIGN PATENT DOCUMENTS

| | | |
|---|---|---|
| CN | 101152081 A | 4/2008 |
| CN | 101828915 A | 9/2010 |
| CN | 102138789 A | 8/2011 |
| CN | 201918016 U | 8/2011 |
| CN | 102347804 A | 2/2012 |
| CN | 105338892 A | 2/2016 |
| DE | 2506936 A1 | 9/1976 |
| DE | 4212670 A1 | 1/1994 |
| EP | 0631226 A1 | 12/1994 |
| EP | 1181888 B1 | 9/2007 |
| EP | 1238633 B1 | 10/2008 |
| EP | 2030565 A1 | 3/2009 |
| EP | 2192526 A2 | 6/2010 |
| EP | 2116183 B1 | 2/2012 |
| EP | 2986204 A1 | 2/2016 |
| EP | 3079571 A1 | 10/2016 |
| EP | 3133984 A1 | 3/2017 |
| FR | 2740426 A1 | 4/1997 |
| GB | 2181554 A | 4/1987 |
| GB | 2408105 A | 5/2005 |
| JP | S59122032 A | 7/1984 |
| JP | S59190742 A | 10/1984 |
| JP | S63072231 A | 4/1988 |
| JP | S63294044 A | 11/1988 |
| JP | H01244328 A | 9/1989 |
| JP | H05167540 A | 7/1993 |
| JP | H06326669 A | 11/1994 |
| JP | 2002191562 A | 7/2002 |
| JP | 2002261731 A | 9/2002 |
| JP | 2003010177 A | 1/2003 |
| JP | 2005295378 A | 10/2005 |
| JP | 2006180899 A | 7/2006 |
| JP | 2008532587 A | 8/2008 |
| JP | 2010166961 A | 8/2010 |
| JP | 2012065073 A | 3/2012 |
| KR | 20100059198 A | 6/2010 |
| MX | 2009011781 A | 5/2011 |
| WO | WO-8200910 A1 | 3/1982 |
| WO | WO-8805282 A1 | 7/1988 |
| WO | WO-9008361 A1 | 7/1990 |
| WO | WO-9206551 A1 | 4/1992 |
| WO | WO-9731437 A1 | 8/1997 |
| WO | WO-9838611 A1 | 9/1998 |
| WO | WO-9944494 A1 | 9/1999 |
| WO | WO-0041620 A1 | 7/2000 |
| WO | WO-0147597 A2 | 7/2001 |
| WO | WO-0157619 A2 | 8/2001 |
| WO | WO-02080762 A1 | 10/2002 |
| WO | WO-03075118 A2 | 9/2003 |
| WO | WO-03094720 A1 | 11/2003 |
| WO | WO-2004037080 A1 | 5/2004 |
| WO | WO-2006001005 A2 | 1/2006 |
| WO | WO-2006021956 A2 | 3/2006 |
| WO | WO-2006090371 A2 | 8/2006 |
| WO | WO-2007014545 A2 | 2/2007 |
| WO | WO-2007088315 A1 | 8/2007 |
| WO | WO-2008005015 A1 | 1/2008 |
| WO | WO-2008066682 A2 | 6/2008 |
| WO | WO-2009112976 A1 | 9/2009 |
| WO | WO-2010025166 A1 | 3/2010 |
| WO | WO-2010099066 A2 | 9/2010 |
| WO | WO-2010108287 A1 | 9/2010 |
| WO | WO-2010113354 A1 | 10/2010 |
| WO | WO-2010144626 A1 | 12/2010 |
| WO | WO-2011006356 A1 | 1/2011 |
| WO | WO-2011008838 A1 | 1/2011 |
| WO | WO-2011014292 A1 | 2/2011 |
| WO | WO-2011022942 A1 | 3/2011 |
| WO | WO-2011040877 A1 | 4/2011 |
| WO | WO-2011040878 A1 | 4/2011 |
| WO | WO-2011113070 A1 | 9/2011 |
| WO | WO-2011137375 A2 | 11/2011 |
| WO | WO-2011156374 A2 | 12/2011 |
| WO | WO-2012046158 A1 | 4/2012 |
| WO | WO-2012108895 A1 | 8/2012 |
| WO | 2012125135 A1 | 9/2012 |
| WO | WO-2012129413 A1 | 9/2012 |
| WO | WO-2012160550 A1 | 11/2012 |
| WO | WO-2013028960 A1 | 2/2013 |
| WO | WO-2013036307 A1 | 3/2013 |
| WO | WO-2013066642 A1 | 5/2013 |
| WO | WO-2013093690 A1 | 6/2013 |
| WO | WO-2013122788 A1 | 8/2013 |
| WO | WO-2013138500 A1 | 9/2013 |
| WO | WO-2013155196 A2 | 10/2013 |
| WO | WO-2013192166 A1 | 12/2013 |
| WO | WO-2014172451 A1 | 10/2014 |
| WO | WO-2016183515 A1 | 11/2016 |

OTHER PUBLICATIONS

Australian Design Awards. Heartplus Micro; printed from website http://www.designawards.com/au; printed on Apr. 12, 2002 • 6 pages.

Bajaj, M.D.; "Event Recording in Ambulatory Patients with Syncopal Events"; University of Kansas; Wichita, Kansas; (no date); pp. 15-18; printed on or before Apr. 14, 2010.

Bluetooth. Headset Profile (HSP), printed from website http://bluetooth.com/English/Technology/Works/Pates/HSP.asgx, printed on May 12, 2010, 1 page.

Bramanti et al., Multichannel telemetric system for biomedical signals via switched telephone lines, Medical and Biological Engineering and Computing, Sep. 1982, vol. 20, No. 5, pp. 653-656.

Burke, "A Micropower Dry-Electrode ECG Preamplifier", IEEE Transactions on Biomedical Engineering, Feb. 2000, vol. 47, No. 2, pp. 155-162.

Card Guard CG-6108 Act Ambulatory Cardiac Telemetry Brochure; Card Guard; The Telemedicine Company: Switzerland; 2006; 2 pages.

Cardiocomm Solutions; Gems Air. (PC based ECG management) printed from website http://www.cardiocommsolutions/com; printed on Mar. 19, 2010; 1 page.

Carpenter and Frontera, Smart-watches: a potential challenger to the implantable loop recorder? Europace, 18:791-793, 2016.

Charuvastra. Transtelephonic Cardiac Event Recording for Arrhythmia Surveillance; printed from website http://tchin.org/resource room/c art• printed on Mar. 26, 2010• 2 pages.

Cheng, Allen C.; "Real-Time Cardiovascular Diseases Detection on a Smartphone"; Departments of Electrical and Computer Engineering, Bioengineering, Neurological Surgery and Computer Science; University of Pittsburgh; Pittsburgh, PA; printed on or before Apr. 14, 2010, 2 pages.

(56) References Cited

OTHER PUBLICATIONS

Chinese Patent Application No. 2013800135500 First Office Action dated Oct. 20, 2015.
Creative. PC-80B Portable ECG Monitor w/sd card extension slot; printed from website www.amazon.com/Portable-Monitor-extension-leather-shipping/dp/B0010jWKUE; printed on Feb. 4, 2010• 5 pages.
Deveau, "Health Care eyes smart phones to heal ills", printed from the website http://www.theQiobeandmail.com on Sep. 17, 2009, 4 pages.
Dinh. Heart activity monitoring on smartphone. IPCBEE-Int. Conf. Biomedical Eng and Technol. Jun. 17-19, 2011. 11:45-49.
Dobrev, et al., Bootstrapped two-electrode biosignal amplifier, Med Bioi Eng Comput, 2008, 7 pages.
Dolan; Qualcomm launches ECG smartphone program in China; Sep. 8, 2011; 11 pgs.; retrieved Mar. 19, 2011; from the internet (http://mobihealthnews.com/13092/qualcomm-launches-ecg-smartphone-program-in-china/).
Elert, Glenn (Editor); Frequency Range of Human Hearing; The Physics Factbook; web version as of Mar. 29, 2010; 2 pgs.; printed Jun. 6, 2012 (http://web.archive.org/web/20100329141847/http:I/hypertextbook.com/facts/2003/ChrisDAmbrose.shtml).
European Patent Application No. 14785223.0 extended European Search Report dated Aug. 23, 2016.
European Search Report and opinion dated Nov. 21, 2014 for EP Application No. 11865699.0.
Favorite Plus. Handheld Easy ECG Monitor—Handheld Easy EKG Monitor; printed from website www.favoriteplus.com/easy-ecg-handgeld-monitor-fp; printed on Feb. 4, 2010; 2 pages.
Favorite Plus. Handheld ECG Monitor—Handheld EKG Monitor at Favoriteplus.com; printed from website www.favoriteplus.com/handheld-ecg-ekg-monitor; printed on Feb. 4, 2010; 3 pages.
Favorite Plus. Handheld ECG Monitor—Handheld EKG Monitor InstantCheck; printed from website http://www. favoriteplus.com/instanchcheck-hand held-ecg-ekg-monitor; printed on Feb. 4, 2010; 2 pages.
Ferrick, M.D.; "Holter Monitoring and cardiac Event Recording in Assessing Symptomatic Patients"; Albert Einstein College of Medicine; Bronx, New York; (no date)• pp. 11-14• printed on or before Apr. 14, 2010.
FREE2MOVE. Vitaphone 2300; www.free2move.us/News/NewsVitaghone 240105.htm printed May 12, 2010.
Fulford-Jones, et al., "A Portable, Low-Power, Wireless Two-Lead EKG System", Division of Engineering and Applied Sciences, Harvard University, Sep. 2004, 4 pages.
Garabelli et al. Accuracy and Novelty of an Inexpensive iPhone-based Event Recorder (Presentation Poster/Abstract) Heart Rhythm 2012, 33rd Annual Scientific Session. SP23. Innovation Poster Session II. No. IA02-1; May 11, 2012.
GBI Portal. Qualcomm's wireless reach mHealth project to improve cardiovascular disease in resource scarce China; Feb. 17, 2012; 7 pgs. Retrieved Mar. 19, 2014 from www.intergrallc.com/2012/02/17/qualcooms-wireless-reach-mhealth-project-to-improve-cardiovascular-disease-in-resource-scarce-china/.
GE; Healthcare., "Marquette heart rate turbulence analysis program", 2005, DC-0160-12.05-EN-US. 4 pages.
Gillette, M.D.; "Diagnosis of Pediatric Arrhythmias with Event Recording"; Medical University of South Carolina; Charleston, South Carolina; (no date); pp. 25-32; printed on or before Apr. 14, 2010.
Grier, James W.; "How to use 1-lead ECG recorders to obtain 12-lead resting ECGs and exercise ("stress") ECGs"; Department of Biological Sciences: printed from website http://www.ndsu.edu/pubweb/rvgrier; printed on Jun. 7, 2010; 13 pages.
Hannaford, Kat; "How to Turn Your iPhone Into a Laser, Fan or Flashlight"; printed from website http://m.qizmodo.com/5534904• printed on Feb. 3, 2011, 2 pages.
Hartmann, "ECG Front-End Design is Simplified with MicroConverter" Analog Dialogue, Nov. 2003, vol. 37, pp. 1-5.
Hayes, M.D.; "Approaches to Diagnosing Transient Arhythmias" An Overview; Mayo Clinic; Rochester Minnesota; (no date); pp. 7-10; printed on or before Apr. 14, 2010.
Hearing Loss Assoc. of Kentuckiana; Decibel Ratings/Hazardous Time Exposures of Common Noise (excerpt from Survivor's Manual); web version as of Oct. 5, 2008; 2 pgs.; printed Jun. 6, 2012 (http://web.archive.org/web/20081005143856/http://www.hearinglossky.orglhlasurvival1.html).
Huang, Tina; Age-related hearing loss; Minnesota Medicine; 90(10); pp. 48-50; Oct. 2007; printed Jun. 6, 2012 from: http://www.minnesotamedicine.com/PastIssues/PastIssues2007/October2007/Ciinca1Huang0ctober2007.aspx).
IMEC News; IMEC extends flexible ECG patch to enable arrhythmia detection; printed from website http://www2.imec.be/imeC' printed on Aug. 18, 2009 1 page.
Instromedix. Cardiac Event Recording FAQ's; Instromedix a Card Guard Company, San Diego, CA.; printed from website www.instromedix.com/pdf/products/cardiac; printed on or before Apr. 14, 2010.
Instromedix. The Arrhythmia Monitoring System; King of Hearts Express AF Recorder Brochure from Instromedix• A CardGuard Company; Rosemont IL; 2004. 3 pages.
International preliminary report on patentability dated Jul. 29, 2014 for PCT/US2013/023370.
International search report and written opinion dated Feb. 12, 2015 for PCT Application No. US2014/054414.
International search report and written opinion dated Feb. 17, 2012 for PCT/US2011/039445.
International search report and written opinion dated Apr. 27, 2012 for PCT/US2011/053708.
International search report and written opinion dated Apr. 30, 2015 for PCT/US2014/070170.
International search report and written opinion dated May 15, 2013 for PCT/US2013/023370.
International search report and written opinion dated Dec. 17, 2013 for PCT/US2013/055458.
International search report dated Sep. 1, 2014 for PCT/US2014/034350.
International search report dated Dec. 10, 2013 for PCT/US2013/057576.
Japanese Patent Application No. 2014-511335 Decision of Rejection dated Jul. 28, 2016.
Japanese Patent Application No. 2014-554916 Office Action dated Sep. 26, 2016.
Jenkins II, W.; Time/Frequency Relationships for an FFT-Based Acoustic Modem; Naval Postgraduate School; pp. 1-102; Sep. 2010 (http://edocs.nps.edu/npspubs/scholarly/theses/2010/Sep/1 OSep_Jenkins.pdf) printed Oct. 2, 2013.
Kim, et al., "Detection of Atrial Fibrillation Episodes using Multiple Heart Rate Variability Features in Different Time Periods." Conference Proceedings IEEE Eng Med Biol Soc EMBS, 30th Annual International Conference, Aug. 20-25, 2008, p. 5482-5485.
Koerner. The Author's Metrics; Wired Magazine Article; New York, NY; Jul. 2009; p. 93-126.
Kumar, M.D., "Zio Patch", printed from website http://www.irhythmtech.com/zio-solution/zio-gach/, grinted on Apr. 12, 2010.
Kumparak, Greg; "Visa officially announces their case that turns your iPhone into a credit card (and we've got pies!)"; May 17, 2010; printed from website www.mobilecrunch.com• printed on Feb. 3, 2011.
Lau, et al. iPhone ECG application for community screening to detect silent atrial fibrillation: A novel technology to prevent stroke. Int J Cardiol. Apr. 30, 2013;165(1):193-4.
Lau, et al. Performance of an Automated iPhone ECG Algorithm to Diagnose Atrial Fibrillation in a Community AF Screening Program (SEARCH-AF). Heart, Lung and Circulation. 2013; 22:S205.
Lau et al. Validation of an iPhone ECG application suitable for community screening for silent atrial fibrillation—A novel way to prevent stroke (Presentation Abstract 16810); American Heart Association 2012 Scientific Sessions and Resuscitation Science Symposium; 126(1); Nov. 20, 2012, 2 pages.

(56) References Cited

OTHER PUBLICATIONS

Leijdekkers et al., "Trial Results of a Novel Cardiac Rhythm Management System using Smart Phones and wireless ECG Sensors", Proceedings of the International Conf. on Smart homes and health Telematics., Jul. 1-3, 2009, Tours, France, 8 pages.

Levkov et al., "Removal of power-line interference from the ECG: a review of the subtraction procedure" BioMedical Engineering Online 2005, printed from website http://www.biomedical-engineeringonline.com/contenU4/1/50 pp. 1-18.

Lin; et al., "An intelligent telecardiology system using a wearable and wireless ECG to detect atrial fibrillation.", May 2010, 14(3), 726-33.

Lowres, et al. Screening Education and Recognition in Community Pharmacies of Atrial Fibrillation to prevent stroke in an ambulant population aged =65 years SEARCH-AF stroke prevention study): a cross-sectional study protocol. BMJ Open. Jun. 25, 2012; 2(3)e001355.

M Med Choice. Handheld ECG Monitor Brochure; M Med Choice, Beijing Choice Electronic Technology Co. Ltd.• published on or before Apr. 14, 2010, 6 pages.

M Med Choice. Handheld ECG Monitor MD100A1; printed from website http://www.choicemmed.com/productshow.as_p; printed on Dec. 28, 2009; 2 pages.

M Med Choice. Handheld ECG Monitor MD10013; printed from website: http://www.choicemmed.com/productshow.asp; printed on Dec. 28, 2009• 2 pages.

M Med Choice printed from website: http://www.choicemmed.con/1xwm.asp; printed on Dec. 28, 2009• 1 page.

MacFarlane, et al. Resting 12-lead ECG electrode placement and associated problems; SCST update 1995; 15pgs. Printed Feb. 18, 2014 from www.scst.org.uk/resources/RESTING_12.pdf.

Mauvila ECG Tutorial; Basic ECG Interpretation Tutorial; Sections 1-12; printed from website http://mauvila.com/ECG/ecg.htm• printed on Mar. 26, 2010. 56 pages.

Medgadget. Zio Patch Wins Medical Design Award.MedGadget internet journal of emerging medical technologies, 2010, 1 page, printed from website: http://medaadaet.com/archives/2010/04/zio_patch_wins_medial_design_award_1.html.

MiCardioMobile: Remote Wireless Cardiac Rehabilitation Monitoring printed from website htto://alivetec.cable.nu/cardiomobile• printed on or before Apr. 14, 2010, 1 page.

Mobility Mind. Use your Treo 650 as a portable ECG monitoring device, Mobility Mind Celebrating mobile Internet lifestyle and culture, Sep. 14, 2005, 1 page. printed from website httg://www.treotoday.net/2005/09/14/use-your-treo-650-as-a-portab le-ecg-monitoring-device/.

Modem Protocols Explained; ftp://kermit.columbia.edu/kermit/cu/protocol.html; 5 pgs.; printed Oct. 2, 2013.

Modem Tutorial; http://www.lsu.edu/OCS/its/unix/tutoriai/ModemTutoriai/ModemTutorial.html; 2 pgs.; printed Oct. 2, 2013.

Muench, Frederick, PhD; "HRV: The Manufacturers and Vendors Speak; The portable StressEraser Heart Rate Variability Biofeedback Device: Background and Research". Biofeedback vol. 36 Issue 1, pp. 35-39• published Spring 2008.

Murph. RedEye mini converts iPhone, iPad or iPod touch into IR-beaming universal remote; printed from website http://www.engadget.com/2010/03/02/redeye; printed on Mar. 2, 2010; 3 pages.

Nam et al.; An Ultrasonic Sensor Based Low-Power Acoustic Modem for Underwater Communication in Underwater Wireless Sensor Networks; Computer Network Lab, Dept. of Elec. Eng., Korea Univ.; pp. 494-504; Dec. 2007 (http://nesl.ee.ucla.edu/fw/torres/home/Dropbox/good_paper_mico_controller.pdf; 11 pgs.; printed Oct. 2, 2013).

Neuroreille; Audiometry; web version as of Oct. 14, 2008; 1 pg.; printed Jun. 6, 2012 (http://www.neuroreille.com/promenade/english/audiometry/audiometry.htm).

New Professional Quality ECGEKG Portable Heart Monitor; printed from website http://cgibay.com/ws/eBayiSAPI.d11• printed on Feb. 4, 2010• 3 pages.

Notice of allowance dated Jan. 8, 2014 for U.S. Appl. No. 14/015,303.

Notice of allowance dated Jan. 27, 2014 for U.S. Appl. No. 14/015,303.
Notice of allowance dated Feb. 26, 2014 for U.S. Appl. No. 14/015,303.
Notice of allowance dated May 23, 2014 for U.S. Appl. No. 13/108,738.
Notice of allowance dated Jul. 9, 2013 for U.S. Appl. No. 12/796,188.
Notice of allowance dated Aug. 28, 2012 for U.S. Appl. No. 13/420,520.
Notice of allowance dated Dec. 4, 2013 for U.S. Appl. No. 14/015,303.
Notice of Allowance dated Jun. 16, 2016 for U.S. Appl. No. 14/569,513.
Notice of Allowance dated Mar. 29, 2016 for U.S. Appl. No. 14/254,310.
Office action dated Jan. 2, 2014 for U.S. Appl. No. 13/108,738.
Office action dated Jun. 18, 2012 for U.S. Appl. No. 13/420,520.
Office action dated Sep. 12, 2014 for U.S. Appl. No. 13/108,738.
Office action dated Oct. 6, 2014 for U.S. Appl. No. 14/252,044.
Office action dated Oct. 29, 2012 for U.S. Appl. No. 12/796,188.
Office action dated Nov. 19, 2014 for U.S. Appl. No. 13/969,446.
Office Action dated Aug. 25, 2015 for U.S. Appl. No. 14/479,105.
Office Action dated Dec. 21, 2015 for U.S. Appl. No. 13/964,490.
Office Action dated Feb. 24, 2016 for U.S. Appl. No. 14/730,122.
Office Action dated Jun. 13, 2016 for U.S. Appl. No. 14/730,122.
Office Action dated May 18, 2015 for U.S. Appl. No. 13/752,048.
Office Action dated Oct. 6, 2015 for U.S. Appl. No. 14/569,513.

Omron Portable ECG EKG Handheld HCG-801 Monitor; printed from website http://www.amazon.com/Omron-Portable-Handheld-HCG-801-Monitor/dp/B0019WH3EO• printed on Feb. 24, 2010• 5 pages.

Omron Portable ECG Monitor; printed from website http://www.target.com/gp/detail.html; printed on Mar. 26, 2010• 1 page.

Oresko, et al., "Detecting Cardiovascular Diseases via Real-Time Electrocardiogram Processing on a Smartphone", 2009 Workshop on Biomedicine in Computing: Systems, Architectures, and Circuits, pp. 13-16.

PCT Patent Application No. PCT/US2014/070170 International Preliminary Report on Patentability dated Jun. 23, 2016.

PCT/US2014/054414 International Preliminary Report on Patentability dated Mar. 17, 2016.

PCT/US2016/032524 International Search Report and Written Opinion dated Aug. 19, 2016.

Perez, Sarah; No NFC? No Problem; New Startup Zoosh Provides Workaround Technology (Jun. 20, 2011 ); printed on or before Jun. 27, 2011 from website; 2 pgs.; (http://www.readwriteweb.com/archives).

Prystowsky, M.D.; "Chairman's Introduction"; Duke University Medical Center; Indianapolis, Indiana• (no date)• pp. 5-6• printed on or before Apr. 14, 2010.

Prystowsky, M.D.; "Chairman's Summary"; Duke University Medical Center; Indianapolis Indiana; (no date); pp. 39-40• printed on or before Apr. 14, 2010.

Prystowsky, M.D., "The Clinical Application, Diagnostic Yield and Cost Considerations of Cardiac Event Recorders", Indianapolis, Indiana (no date) pp. 19-23. printed on or before Apr. 14, 2010.

Puurtinen, et al., Best Electrode Locations for a Small Bipolar ECG Device: Signal Strength Analysis of Clinical Data, Annals of Biomedical Engineering, vol. 37, No. 2, Feb. 2009 ( © ) 2008) pp. 331-336.

Raju Heart-Rate and EKG Monitor Using the MSP430FG439, SLAA280—Oct. 2005—Revised Sep. 2007, 11 pages.

Read-My-Heart. ECG Machine Handheld Read MyHeart; (product item No. HH-3413) printed from website http://www.helioliving.com/ECG-Machine-Handheld-ReadMyHeart; printed on Feb. 4, 2010; 1 page.

Read-My-Heart Personal Handheld ECG Monitor with Free Illustrator Book & Free Electrodes V2.2; printed from website http://www.amazon.com/Readmyheart-Personai-Handheld-illustrator-Eiectrodes/dp/B0010AN63W; printed on Mar. 26, 2010; 4 pages.

Ricker. Square payment dongle demoed for iPhone toting hippies and you (video); printed from website http://www.engadget.com/2010/01/18/square-payment; printed on Jan. 18, 2010; 6 pages.

(56) References Cited

OTHER PUBLICATIONS

Rockwood. The Networked Body Magazine Article from FAST TALK Magazine; Jul./Aug. 2009; pp. 19-26.
Salahuddin, et al., "Ultra Short Term Analysis of Heart Rate Variability using Normal Sinus Rhythm and Atrial Fibrillation ECG Data", Engineering in Medicine and Biology Society, Aug. 2007, pp. 4656-4659.
Saxon, et al. iPhone rhythm strip—the implications of wireless and ubiquitous heart rate monitoring. JACC; 59(13): E726; Mar. 2012.
Saxon. Ubiquitous Wireless ECG Recording: A Powerful Tool Physicians Should Embrace. J Cardiovasc Electrophysiol. 24(4):480-483; Apr. 2013.
Semler, M.D.; "The Future of Cardiac Event Monitoring"; St. Vincent Hospital and Medical Center; Portland Oregon; (no date); pp. 33-37; printed on or before Apr. 14, 2010.
SFO Medical. Choice Portable Handheld ECG EKG Monitor; printed from website http://www.amazon.com/Choice-Portable-Handheld-ECG-Monitor/dp/B001Q74VOM; printed on Mar. 26, 2010; 1 page.
Shenzhen New Element Med. Equipment. Wireless ECG Monitoring System, printed from website http://www.alibaba.com/product-gs/248168581/Wireless_ECG_Monitoring_system.html., printed on Mar. 26, 2010, 2 pages.
Shumaker, J.; Designing an Ultrasonic Modem for Robotic Communications; Army Research Laboratory; 26 pgs.; Mar. 2009 (http://www.dtic.mil/cgi-bin/GetTRDoc?AD=ADA499556) printed Oct. 2, 2013.
Smith. Smartphone may keep the cardiologist away, The Independent, Health & Families, Mar. 5, 2010, printed from website http://www.independent.co.uk/life-style/health-and-families/healthnews/smartghone-may-keep-the-cardiologist-away-1916652.html, printed on Mar. 26, 2010.
Stevens, "Apple's Seamlessly Embedded Heart Rate Monitor could turn the iPhone into a new-age mood ring", printed from the website http://www.enaadaet.com on May 6, 2010, 3 pages.
Taleb Medical. Observer Hand-held ECG Monitor MD100B; (no date); printed on or before Apr. 14, 2010, 1 page.
Tei, et al., New index of combined systolic and diastolic myocardial performance: a simple and reproducible measure of cardiac function—a study in normal and dilated cardiomyopathy; J Cardiol.; 26(6):357-366; Dec. 1995.
Texas Instruments. Information for Medical Applications, "Biophysical Monitoring—Electrocardiogram (ECG) Front End", Apr. 2004, 2 pages.
Tschida. Power A's New Case Turns Your iPhone Into a Universal Remote; printed from website http://appadvice.com/appnn; printed on Mar. 1, 2010• 2 pages.
U.S. Appl. No. 14/479,105 Office Action dated Jul. 22, 2016.
U.S. Appl. No. 14/494,191 Office Action dated Jul. 20, 2016.
U.S. Appl. No. 14/730,122 Notice of Allowance dated Dec. 6, 2016.
Vanhemert, Kyle; "XWave Headset Lets You Control iPhone Apps With Your BRAIN"; Sep. 8, 2010; printed from website http://gizmodo.com; printed on Sep. 8, 2010, 4 pages.
Vitaphone. Telemedicine since 1999: Modern health management is our special subject. 3 pgs. Retrieved Mar. 19, 2014 from www.vitaphone.de/en/company/history-of-vitaphone/.
Wikimedia Laboratories; Acoustics; web archive version dated Jan. 25, 2009; 2 pgs.; printed Jun. 6, 2012 (http://liveweb.archive.org/http://en.labs.wikimedia.org/wiki/Acoustics).
Wikipedia; Aliasing; web version as of Apr. 3, 2011; S pgs.; printed Jun. 6, 2012 (http://liveweb.archive.org/http://en.wikipedia.org/w/index.php?title=Aiiasing&oldid=422141882).
Wikipedia; Hearing Range; web version as of Feb. 6, 2010; 5 pgs.; printed Jun. 6, 2012 (http://web.archive.org/web/201 002062137 41/http://en.wikipedia.org/wiki/Hearing_range).
Wikipedia."Pulse oximetry", printed from website httg://en.wikigedia.orq on May 10, 2010, 4 pages.
Wisneski, C.; Ultrasonic Local Area Communication; http://alumni.media.mit.edu/-wiz/ultracom.html; 2 pgs.; printed Oct. 2, 2013.
Woodward et al; "Bio-Potentiai-To-Frequency Converter/Modulator"; Electronic Design• Aug. 1999• p. 117.
Ziegler, Chris; "EPI Life phone sports ECG function, can let doctors know if you're gonna make it"; printed from website www.enoadoet.com/2010/06/; Jun. 17 2010, 3 pages.
U.S. Appl. No. 15/140,072 Office Action dated Dec. 23, 2016.
European Patent Application No. 11793020.6 extended European Search Report dated Jan. 10, 2017.
European Patent Application No. 11865699.0 Communication dated Dec. 19, 2016.
U.S. Appl. No. 13/964,490 Notice of Allowance dated Jan. 6, 2017.
Chinese Patent Application No. 2014800331017 Office Action dated May 16, 2017.
European Patent Application No. 14869033.2 extended European Search Report dated Jul. 5, 2017.
U.S. Appl. No. 14/692,563 Office Action dated Jun. 29, 2017.
U.S. Appl. No. 15/154,849 Office Action dated Feb. 17, 2017.

\* cited by examiner

METHODS AND SYSTEMS FOR ARRHYTHMIA TRACKING AND SCORING

CROSS-REFERENCE

This application is a divisional of U.S. application Ser. No. 14/730,122, filed Jun. 3, 2015, which is a continuation of U.S. application Ser. No. 14/569,513 filed Dec. 12, 2014, now U.S. Pat. No. 9,420,956, issued Aug. 23, 2016, which claims the benefit of U.S. Provisional Application No. 61/915,113, filed Dec. 12, 2013, which application is incorporated herein by reference, U.S. Provisional Application No. 61/953,616 filed Mar. 14, 2014, U.S. Provisional Application No. 61/969,019, filed Mar. 21, 2014, U.S. Provisional Application No. 61/970,551 filed Mar. 26, 2014 which application is incorporated herein by reference, and U.S. Provisional Application No. 62/014,516, filed Jun. 19, 2014, which application is incorporated herein by reference.

BACKGROUND

The present disclosure relates to medical devices, systems, and methods. In particular, the present disclosure relates to methods and systems for managing health and disease such as cardiac diseases including arrhythmia and atrial fibrillation.

Cardiovascular diseases are the leading cause of death in the world. In 2008, 30% of all global death can be attributed to cardiovascular diseases. It is also estimated that by 2030, over 23 million people will die from cardiovascular diseases annually. Cardiovascular diseases are prevalent in the populations of high-income and low-income countries alike.

Arrhythmia is a cardiac condition in which the electrical activity of the heart is irregular or is faster (tachycardia) or slower (bradycardia) than normal. Although many arrhythmias are not life-threatening, some can cause cardiac arrest and even sudden cardiac death. Atrial fibrillation is the most common cardiac arrhythmia. In atrial fibrillation, electrical conduction through the ventricles of heart is irregular and disorganized. While atrial fibrillation may cause no symptoms, it is often associated with palpitations, shortness of breath, fainting, chest, pain or congestive heart failure. Atrial fibrillation is also associated with atrial clot formation, which is associated with clot migration and stroke.

Atrial fibrillation is typically diagnosed by taking an electrocardiogram (ECG) of a subject, which shows a characteristic atrial fibrillation waveform To treat atrial fibrillation, a patient may take medications to slow heart rate or modify the rhythm of the heart. Patients may also take anticoagulants to prevent atrial clot formation and stroke. Patients may even undergo surgical intervention including cardiac ablation to treat atrial fibrillation.

Often, a patient with arrhythmia or atrial fibrillation is monitored for extended periods of time to manage the disease. For example, a patient may be provided with a Holter monitor or other ambulatory electrocardiography device to continuously monitor a patient's heart rate and rhythm for at least 24 hours.

Current ambulatory electrocardiography devices such as Holter monitors, however, are typically bulky and difficult for subjects to administer without the aid of a medical professional. For example, the use of Holter monitors requires a patient to wear a bulky device on their chest and precisely place a plurality of electrode leads on precise locations on their chest. These requirements can impede the activities of the subject, including their natural movement, bathing, and showering. Once an ECG is generated, the ECG is sent to the patient's physician who may analyze the ECG and provide a diagnosis and other recommendations. Currently, this process often must be performed through hospital administrators and health management organizations and many patients do not receive feedback in an expedient manner.

SUMMARY

Disclosed herein are devices, systems, and methods for managing health and disease such as cardiac diseases, including arrhythmia and atrial fibrillation. In particular, a cardiac disease and/or rhythm management system, according to aspects of the present disclosure, allows a user to conveniently document their electrocardiograms (ECG) and other biometric data and receive recommendation(s) and/or goal(s) generated by the system or by a physician in response to the documented data. The cardiac disease and/or rhythm management system can be loaded onto a local computing device of the user, where biometric data can be conveniently entered onto the system while the user may continue to use the local computing device for other purposes. A local computing device may comprise, for example, a computing device worn on the body (e.g. a head-worn computing device such as a Google Glass, a wrist-worn computing device such as a Samsung Galaxy Gear Smart Watch, etc.), a tablet computer (e.g. an Apple iPad, an Apple iPod, a Google Nexus tablet, a Samsung Galaxy Tab, a Microsoft Surface, etc.), a smartphone (e.g. an Apple iPhone, a Google Nexus phone, a Samsung Galaxy phone, etc.)

A portable computing device or an accessory thereof may be configured to continuously measure one or more physiological signals of a user. The heart rate of the user may be continuously measured. The continuously measurement may be made with a wrist or arm band or a patch in communication with the portable computing device. The portable computing device may have loaded onto (e.g. onto a non-transitory computer readable medium of the computing device) and executing thereon (e.g. by a processor of the computing device) an application for one or more of receiving the continuously measured physiological signal(s), analyzing the physiological signal(s), sending the physiological signal(s) to a remote computer for further analysis and storage, and displaying to the user analysis of the physiological signal(s). The heart rate may be measured by one or more electrodes provided on the computing device or accessory, a motion sensor provided on the computing device or accessory, or by imaging and lighting sources provided on the computing device or accessory. In response to the continuous measurement and recordation of the heart rate of the user, parameters such as heart rate (HR), heart rate variability (R-R variability or HRV), and heart rate turbulence (HRT) may be determined. These parameters and further parameters may be analyzed to detect and/or predict one or more of atrial fibrillation, tachycardia, bradycardia, bigeminy, trigeminy, or other cardiac conditions. A quantitative heart health score may also be generated from the determined parameters. One or more of the heart health score, detected heart conditions, or recommended user action items based on the heart health score may be displayed to the user through a display of the portable computing device.

The biometric data may be uploaded onto a remote server where one or more cardiac technicians or cardiac specialists may analyze the biometric data and provide ECG interpretations, diagnoses, recommendations such as lifestyle recommendations, and/or goals such as lifestyle goals for subject. These interpretations, diagnoses, recommendations, and/or goals may be provided to the subject through the cardiac disease and/or rhythm management system on their local computing device. The cardiac disease and/or rhythm management system may also include tools for the subject to track their biometric data and the associated interpretations, diagnoses, recommendations, and/or goals from the cardiac technicians or specialists.

An aspect of the present disclosure includes a dashboard centered around arrhythmia or atrial fibrillation tracking. The dashboard includes a heart score that can be calculated in response to data from the user such as their ECG and other personal information such as age, gender, height, weight, body fat, disease risks, etc. The main driver of this heart score will often be the incidence of the user's atrial fibrillation. Other drivers and influencing factors include the aforementioned personal information. The heart score will be frequently related to output from a machine learning algorithm that combines and weights many if not all of influencing factors.

The dashboard will often display and track many if not all of the influencing factors. Some of these influencing factors may be entered directly by the user or may be input by the use of other mobile health monitoring or sensor devices. The user may also use the dashboard as an atrial fibrillation or arrhythmia management tool to set goals to improve their heart score.

The dashboard may also be accessed by the user's physician (e.g. the physician prescribing the system to the user, another regular physician, or other physician) to allow the physician to view the ECG and biometric data of the user, view the influencing factors of the user, and/or provide additional ECG interpretations, diagnoses, recommendations, and/or goals.

Another aspect of the present disclosure provides a method for managing cardiac health. Biometric data of a user may be received. A cardiac health score may be generated in response to the received biometric data. One or more recommendations or goals for improving the generated cardiac health score may be displayed to the user. The biometric data may comprise one or more of an electrocardiogram (ECG), dietary information, stress level, activity level, gender, height, weight, age, body fat percentage, blood pressure, results from imaging scans, blood chemistry values, or genotype data. The recommendations or goals may be updated in response to the user meeting the displayed recommendations or goals. The user may be alerted if one or more recommendations or goals have not been completed by the user, for example if the user has not completed one or more recommendations or goals for the day.

The analysis applied may be through one or more of the generation of a heart health score or the application of one or more machine learning algorithms. The machine learning algorithms may be trained using population data of heart rate. The population data may be collected from a plurality of the heart rate monitoring enabled portable computing devices or accessories provided to a plurality of users. The training population of users may have been previously identified as either having atrial fibrillation or not having atrial fibrillation prior to the generation of data for continuously measured heart rate. The data may be used to train the machine learning algorithm to extract one or more features from any continuously measured heart rate data and identify atrial fibrillation or other conditions therefrom. After the machine learning algorithm has been trained, the machine learning algorithm may recognize atrial fibrillation from the continuously measured heart rate data of a new user who has not yet been identified as having atrial fibrillation or other heart conditions. One or more of training population data or the trained machine learning algorithm may be provided on a central computing device (e.g. be stored on a non-transitory computer readable medium of a server) which is in communication with the local computing devices of the users and the application executed thereon (e.g. through an Internet or an intranet connection.)

A set of instructions for managing cardiac health may be downloaded from the Internet. These set of instructions may be configured to automatically generate the cardiac health score. The cardiac health score may be generated using a machine learning algorithm. The machine learning algorithm may generate the cardiac health score of the user and/or the recommendations and/or goals in response to biometric data from a plurality of users. The set of instructions may be configured to allow a medical professional to access the received biometric data. The cardiac health score and/or the recommendations and/or goals may be generated by the medical professional.

The set of instructions may be stored on a non-transitory computer readable storage medium of one or more of a body-worn computer, a tablet computer, a smartphone, or other computing device. These set of instructions may be capable of being executed by the computing device. When executed, the set of instructions may cause the computing device to perform any of the methods described herein, including the method for managing cardiac health described above.

Another aspect of the present disclosure provides a system for managing cardiac health. The system may comprise a sensor for recording biometric data of a user and a local computing device receiving the biometric data from the sensor. The local computing device may be configured to display a cardiac health score and one or more recommendations or goals for the user to improve the cardiac health score in response to the received biometric data.

The system may further comprise a remote server receiving the biometric data from the local computing device. One or more of the local computing device or the remote server may comprise a machine learning algorithm which generates one or more of the cardiac health score or the one or more recommendations or goals for the user. The remote server may be configured for access by a medical professional. Alternatively or in combination, one or more of the cardiac health score or one or more recommendations or goals may be generated by the medical professional and provided to the local computing device through the remote server.

The sensor may comprise one or more of a hand-held electrocardiogram (ECG) sensor, a wrist-worn activity sensor, a blood pressure monitor, a personal weighing scale, a body fat percentage sensor, a personal thermometer, a pulse oximeter sensor, or any mobile health monitor or sensor. Often, the sensor is configured to be in wireless communication with the local computing device. The local computing device comprises one or more of a personal computer, a laptop computer, a palmtop computer, a tablet computer, a smartphone, a body-worn computer, or the like. The biometric data may comprise one or more of an electrocardiogram (ECG), dietary information, stress level, activity level, gender, height, weight, age, body fat percentage, or blood pressure.

Other physiological signals or parameters such as physical activity, heart sounds, blood pressure, blood oxygenation, blood glucose, temperature, activity, breath composition, weight, hydration levels, an electroencephalograph (EEG), an electromyography (EMG), a mechanomyogram (MMG), an electrooculogram (EOG), etc. may also be monitored. The user may also input user-related health data such as age, height, weight, body mass index (BMI), diet, sleep levels, rest levels, or stress levels. One or more of these physiological signals and/or parameters may be combined with the heart rate data to detect atrial fibrillation or other conditions. The machine learning algorithm may be configured to identify atrial fibrillation or other conditions in response to heart rate data in combination with one or more of the other physiological signals and/or parameters for instance. Triggers or alerts may be provided to the user in response to the measured physiological signals and/or parameters. Such triggers or alerts may notify the user to take corrective steps to improve their health or monitor other vital signs or physiological parameters. The application loaded onto and executed on the portable computing device may provide a health dash board integrating and displaying heart rate information, heart health parameters determined in response to the heart rate information, other physiological parameters and trends thereof, and recommended user action items or steps to improve health.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the subject matter disclosed herein are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Devices, systems, and methods for managing health and disease such as cardiac diseases, including arrhythmia and atrial fibrillation, are disclosed. In particular, a cardiac disease and/or rhythm management system, according to aspects of the present disclosure, allows a user to conveniently document their electrocardiograms (ECG) and other biometric data and receive recommendation(s) and/or goal(s) generated by the system or by a physician in response to the documented data.

The term "atrial fibrillation," denoting a type of cardiac arrhythmia, may also be abbreviated in either the figures or description herein as "AFIB."

Figure 1:
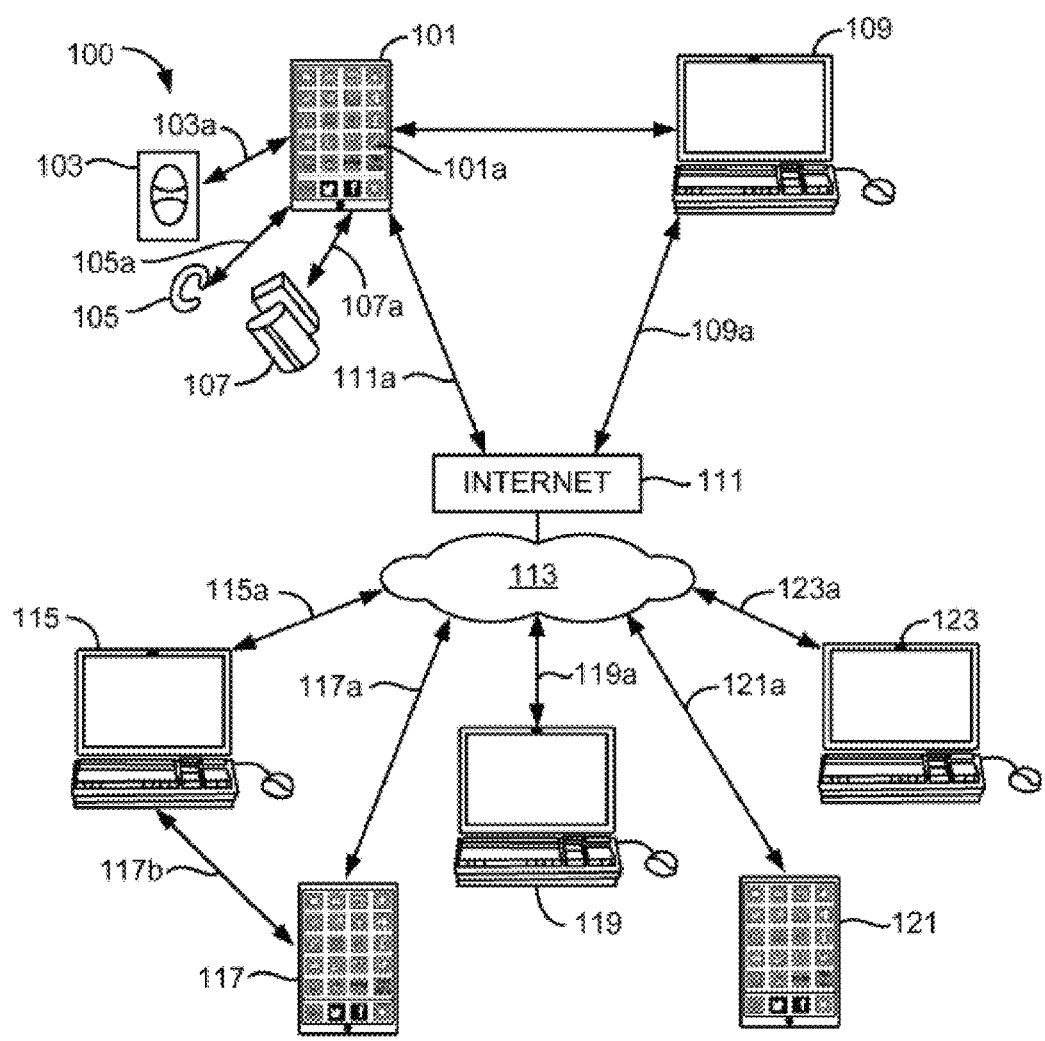
FIG. 1 shows a system for cardiac disease and rhythm management.

FIG. 1 shows a system 100 for cardiac disease and rhythm management. The system 100 may be prescribed for use by a user or subject such as being prescribed by the user or subject's regular or other physician or doctor. The system 100 may comprise a local computing device 101 of the user or subject. The local computing device 101 may be loaded with a user interface, dashboard, or other sub-system of the cardiac disease and rhythm management system 100. For example, the local computing device 101 may be loaded with a mobile software application ("mobile app") 101a for interfacing with the system 100. The local computing device may comprise a computing device worn on the body (e.g. a head-worn computing device such as a Google Glass, a wrist-worn computing device such as a Samsung Galaxy Gear Smart Watch, etc.), a tablet computer (e.g. an Apple iPad, an Apple iPod, a Google Nexus tablet, a Samsung Galaxy Tab, a Microsoft Surface, etc.), a smartphone (e.g. an Apple iPhone, a Google Nexus phone, a Samsung Galaxy phone, etc.).

The local computing device 101 may be coupled to one or more biometric sensors. For example, the local computing device 101 may be coupled to a handheld ECG monitor 103. The handheld ECG monitor 103 may be in the form of a smartphone case as described in co-owned U.S. patent application Ser. No. 12/796,188 (now U.S. Pat. No. 8,509,882), Ser. Nos. 13/107,738, 13/420,520 (now U.S. Pat. No. 8,301,232), Ser. Nos. 13/752,048, 13/964,490, 13/969,446, 14/015,303, and 14/076,076, the contents of which are incorporated herein by reference.

In some embodiments, the handheld ECG monitor 103 may be a handheld sensor coupled to the local computing device 101 with an intermediate protective case/adapter as described in U.S. Provisional Application No. 61/874,806, filed Sep. 6, 2013, the contents of which are incorporated herein by reference. The handheld ECG monitor 103 may be used by the user to take an ECG measurement which the handheld ECG monitor 103 may send to the local computing device by connection 103a. The connection 103a may comprise a wired or wireless connection (e.g. a WiFi connection, a Bluetooth connection, a NFC connection, an ultrasound signal transmission connection, etc.). The mobile software application 101a may be configured to interface with the one or more biometric sensors including the handheld ECG monitor 103.

The local computing device 101 may be coupled to a wrist-worn biometric sensor 105 through a wired or wireless connection 105a (e.g. a WiFi connection, a Bluetooth connection, a NFC connection, an ultrasound signal transmission connection, etc.). The wrist-worn biometric sensor 105 may comprise an activity monitor such as those available from Fitbit Inc. of San Francisco, Calif. or a Nike FuelBand available from Nike, Inc. of Oregon. The wrist-worn biometric sensor 105 may also comprise an ECG sensor such as that described in co-owned U.S. Provisional Application No. 61/872,555, the contents of which is incorporated herein by reference.

The local computing device 101 may be coupled to other biometric devices as well such as a personal scale or a blood pressure monitor 107. The blood pressure monitor 107 may communicate with the local device 101 through a wired or wireless connection 107a (e.g. a WiFi connection, a Bluetooth connection, a NFC connection, an ultrasound signal transmission connection, etc.).

The local computing device 101 may directly communicate with a remote server or cloud-based service 113 through the Internet 111 via a wired or wireless connection 111a (e.g. a WiFi connection, a cellular network connection, a DSL Internet connection, a cable Internet connection, a fiber optic Internet connection, a T1 Internet connection, a T3 Internet connection, etc.). Alternatively or in combination, the local computing device 101 may first couple with another local computing device 109 of the user, such as a personal computer of the user, which then communicates with the remote server or cloud-based service 113 via a wired or wireless connection 109a (e.g. a WiFi connection, a cellular network connection, a DSL Internet connection, a cable Internet connection, a fiber optic Internet connection, a T1 Internet connection, a T3 Internet connection, etc.) The local computing device 109 may comprise software or other interface for managing biometric data collected by the local computing device 101 or the biometric data dashboard loaded on the local computing device 101.

Other users may access the patient data through the remote server or cloud-based service 113. These other users may include the user's regular physician, the user's prescribing physician who prescribed the system 100 for use by the user, other cardiac technicians, other cardiac specialists, and system administrators and managers. For example, a first non-subject user may access the remote server or cloud-based service 113 with a personal computer or other computing device 115 through an Internet connection 115a (e.g. a WiFi connection, a cellular network connection, a DSL Internet connection, a cable Internet connection, a fiber optic Internet connection, a T1 Internet connection, a T3 Internet connection, etc.). Alternatively or in combination, the first non-subject user may access the remote server or cloud-based service 113 with a local computing device such as a tablet computer or smartphone 117 through an Internet connection 117a. The tablet computer or smartphone 117 of the first non-subject user may interface with the personal computer 115 through a wired or wireless connection 117b (e.g. a WiFi connection, a Bluetooth connection, a NFC connection, an ultrasound signal transmission connection, etc.). Further, a second non-subject user may access the remote server or cloud-based service 113 with a personal computer or other computing device 119 through an Internet connection 119a (e.g. a WiFi connection, a cellular network connection, a DSL Internet connection, a cable Internet connection, a fiber optic Internet connection, a T1 Internet connection, a T3 Internet connection, etc.). Further, a third non-subject user may access the remote server or cloud-based service 113 with a tablet computer or smartphone 121 through an Internet connection 121a (e.g. a WiFi connection, a cellular network connection, a DSL Internet connection, a cable Internet connection, a fiber optic Internet connection, a T1 Internet connection, a T3 Internet connection, etc.). Further, a fourth non-subject user may access the remote server or cloud-based service 113 with a personal computer or other computing device 123 through an Internet connection 123a (e.g. a WiFi connection, a cellular network connection, a DSL Internet connection, a cable Internet connection, a fiber optic Internet connection, a T1 Internet connection, a T3 Internet connection, etc.). The first non-subject user may comprise an administrator or manager of the system 100. The second non-subject user may comprise a cardiac technician. The third non-subject user may comprise a regular or prescribing physician of the user or subject. And, the fourth non-subject user may comprise a cardiac specialist who is not the user or subject's regular or prescribing physician. Generally, many if not all of the communication between various devices, computers, servers, and cloud-based services will be secure and HIPAA-compliant.

Aspects of the present disclosure provide systems and methods for detecting and/or predicting atrial fibrillation or other arrhythmias of a user by applying one or more machine learning-based algorithms. A portable computing device (or an accessory usable with the portable computing device) may provide R-R intervals and/or raw heart rate signals as input to an application loaded and executed on the portable computing device. The raw heart rate signals may be provided using an electrocardiogram (ECG) in communication with the portable computing device or accessory such as described in U.S. Ser. No. 13/964,490 filed Aug. 12, 2013, Ser. No. 13/420,520 filed Mar. 14, 2013, Ser. No. 13/108,738 filed May 16, 2011, and Ser. No. 12/796,188 filed Jun. 8, 2010. Alternatively or in combination, the raw heart rate signals may be provided using an on-board heart rate sensor of the portable computing device or by using photoplethysmography implemented by an imaging source and a light source of the portable computing device. Alternatively or in combination, the raw heart rate signals may be from an accessory device worn by the user or attached to the user (e.g. a patch) and which is in communication with the portable computing device. Such wearable accessory devices may include Garmin's Vivofit Fitness Band, Fitbit, Polar Heart Rate Monitors, New Balance's Balance Watch, Basis B1 Band, MIO Alpha, Withings Pulse, LifeCORE Heart Rate Monitor strap, and the like.

R-R intervals may be extracted from the raw heart rate signals. The R-R intervals may be used to calculate heart rate variability (HRV) which may be analyzed in many ways such as using time-domain methods, geometric methods, frequency-domain methods, non-linear methods, long term correlations, or the like as known in the art. Alternatively or in combination, the R-R intervals may be used for non-traditional measurements such as (i) determining the interval between every other or every three R-waves to evaluate for bigeminy or trigeminy or (ii) the generation of a periodic autoregressive moving average (PARMA).

The machine learning based algorithm(s) may allow software application(s) to identify patterns and/or features of the R-R interval data and/or the raw heart rate signals or data to predict and/or detect atrial fibrillation or other arrhythmias. These extracted and labelled features may be features of HRV as analyzed in the time domain such as SDNN (the standard deviation of NN intervals calculated over a 24 hour period), SDANN (the standard deviation of the average NN intervals calculated over short periods), RMSSD (the square root of the mean of the sum of the squares of the successive differences between adjacent NNs), SDSD (the standard deviation of the successive differences between adjacent NNs), NN50 (the number of pairs of successive NNs that differ by more than 50 ms), pNN50 (the proportion of NN50 divided by total number of NNs), NN20 (the number of pairs of successive NNs that differ by more than 20 ms), pNN20 (the proportion of NN20 divided by the total number of NNs), EBC (estimated breath cycle), NNx (the number of pairs of successive NNs that differ by more than x ms), pNNx (the proportion of NNx divided by the number of NNs), or other features known in the art. Alternatively or in combination, the extracted and labelled features may comprise a nonlinear transform of R-R ratio or R-R ratio statistics with an adaptive weighting factor. Alternatively or in combination, the extracted and labelled features may be features of HRV as analyzed geometrically such as the sample density distribution of NN interval durations, the sample density distribution of differences between adjacent NN intervals, a Lorenz plot of NN or RR intervals, degree of skew of the density distribution, kurtosis of the density distribution, or other features known in the art. Alternatively or in combination, the extracted and labelled features may be features of HRV in the frequency domain such as the power spectral density of different frequency bands including a high frequency band (HF, from 0.15 to 0.4 Hz), low frequency band (LF, from 0.04 to 0.15 Hz), and the very low frequency band (VLF, from 0.0033 to 0.04 Hz), or other frequency domain features as known in the art. Alternatively or in combination, the extracted and labelled features may be non-linear features such as the geometric shapes of a Poincaré plot, the correlation dimension, the nonlinear predictability, the pointwise correlation dimension, the approximate entropy, and other features as known in the art. Other features from the raw heart rate signals and data may also be analyzed. These features include for example a generated autoregressive (AR) model, a ratio of consecutive RR intervals, a normalized ratio of consecutive RR intervals, a standard deviation of every 2, 3, or 4 RR intervals, or a recurrence plot of the raw HR signals, among others.

The features of the analysis and/or measurement may be selected, extracted, and labelled to predict atrial fibrillation or other arrhythmias in real time, e.g. by performing one or more machine learning operation. Such operations can be selected from among an operation of ranking the feature(s), classifying the feature(s), labelling the feature(s), predicting the feature(s), and clustering the feature(s). Alternatively or in combination, the extracted features may be labelled and saved for offline training of a machine learning algorithm or set of machine learning operations. For example, the operations may be selected from any of those above. Any number of machine learning algorithms or methods may be trained to identify atrial fibrillation or other conditions such as arrhythmias. These may include the use of decision tree learning such as with a random forest, association rule learning, artificial neural network, inductive logic programming, support vector machines, clustering, Bayesian networks, reinforcement learning, representation learning, similarity and metric learning, sparse dictionary learning, or the like.

The systems and methods for detecting and/or predicting atrial fibrillation or other conditions such as arrhythmias described herein may be implemented as software provided as a set of instructions on a non-transitory computer readable medium. A processor of a computing device (e.g. a tablet computer, a smartphone, a smart watch, a smart band, a wearable computing device, or the like) may execute this set of instructions to receive the input data and detect and/or predict atrial fibrillation therefrom. The software may be downloaded from an online application distribution platform such as the Apple iTunes or App Store, Google Play, Amazon App Store, and the like. A display of the computing device may notify the user whether atrial fibrillation or other arrhythmias has been detected and/or if further measurements are required (e.g. to perform a more accurate analysis). The software may be loaded on and executed by the portable computing device of the user such as with the processor of the computing device.

The machine learning-based algorithms or operations for predicting and/or detecting atrial fibrillation or other arrhythmias may be provided as a service from a remote server which may interact or communicate with a client program provided on the computing device of the user, e.g. as a mobile app. The interaction or communication may be through an Application Program Interface (API). The API may provide access to machine learning operations for ranking, clustering, classifying, and predicting from the R-R interval and/or raw heart rate data, for example.

The machine learning-based algorithms or operations, provided through a remote server and/or on a local application on a local computing device, may operate on, learn from, and make analytical predictions from R-R interval data or raw heart rate data, e.g. from a population of users. The R-R interval or raw heart rate data may be provided by the local computing device itself or an associated accessory, such as described in U.S. Ser. No. 13/964,490 filed Aug. 12, 2013, Ser. No. 13/420,520 filed Mar. 14, 2013, Ser. No. 13/108,738 filed May 16, 2011, and Ser. No. 12/796,188 filed Jun. 8, 2010. Thus, atrial fibrillation and other arrhythmias or other heart conditions can be in a convenient, user-accessible way.

Figure 2:
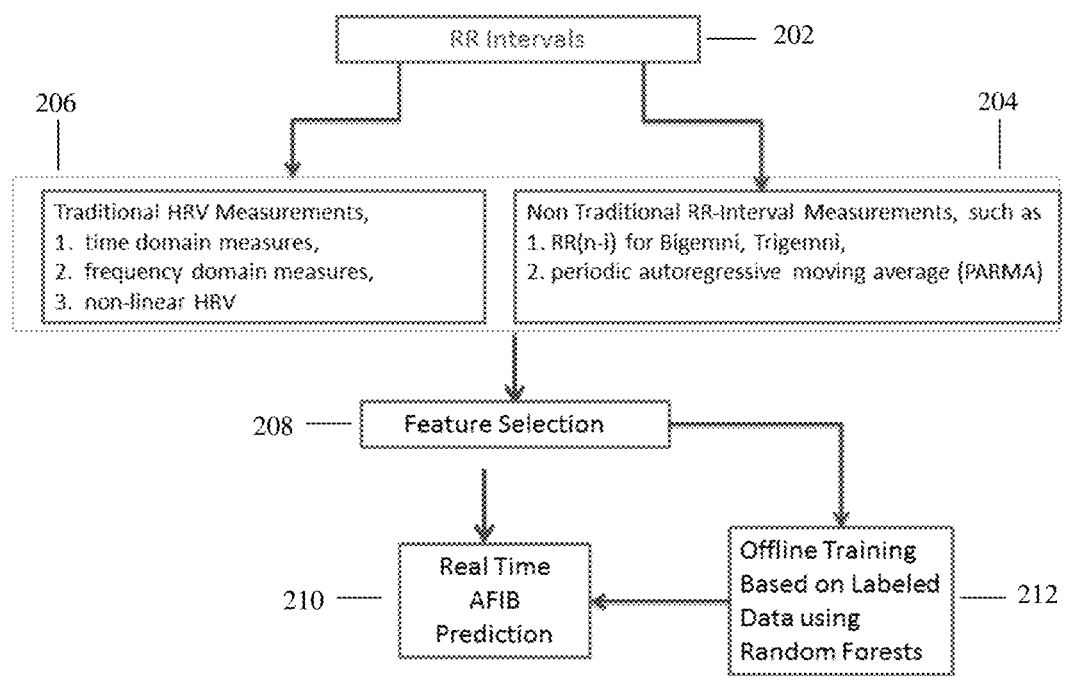
FIG. 2 shows a flow chart of a method 200 for predicting and/or detecting atrial fibrillation from R-R interval measurements.

FIG. 2 shows a flow chart of a method 200 for predicting and/or detecting atrial fibrillation from R-R interval measurements. In a step 202, an R-R interval of a user is obtained. In a step 204, the obtained R-R interval is analyzed using one or more traditional heart rate variability measurements such as, for example, time domain measures, frequency domain measures, and non-linear heart rate variability. In a step 206, the obtained R-R interval is analyzed using one or more non-traditional heart rate variability measurements such as, for example, RR (n-i) for Bigeminy and Trigeminy detection, and the generation of a periodic autoregressive moving average (PARMA). In a step 208, a feature selection occurs. In a step 210, a real time prediction or detection of atrial fibrillation, and/or in a step 212, the heart rate variability measurements may be labelled and saved for offline training of a machine learning algorithm or set of machine learning operations, and then may be subsequently used to make a real time prediction and/or detection of atrial fibrillation.

Figure 3:
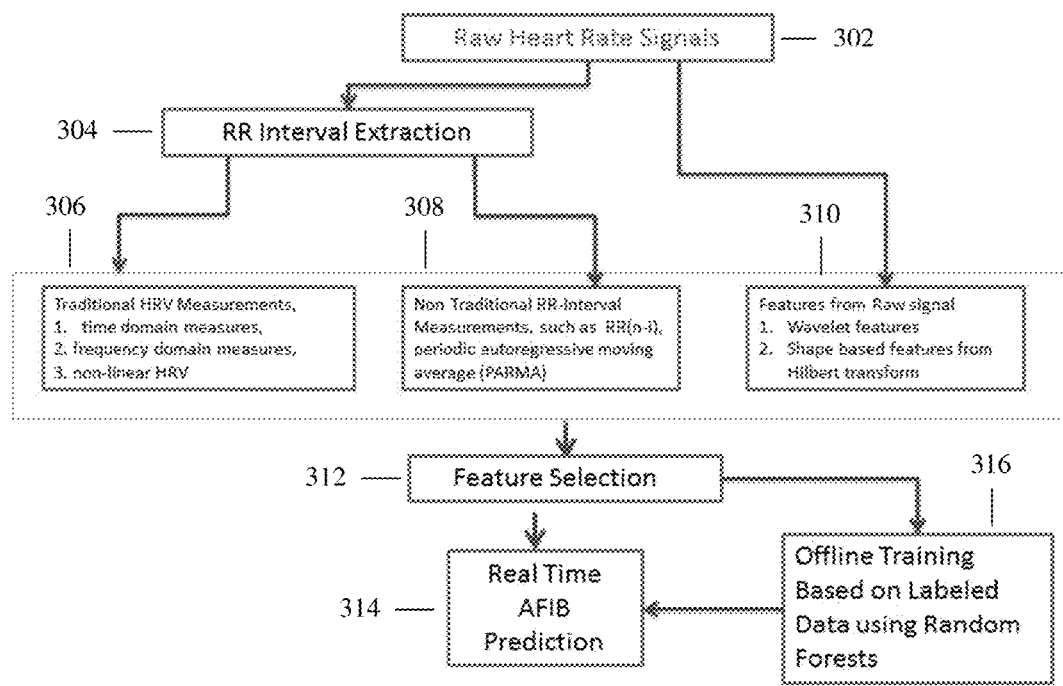
FIG. 3 shows a flow chart of a method for predicting and/or detecting atrial fibrillation from R-R interval measurements and for predicting and/or detecting atrial fibrillation from raw heart rate signals.

FIG. 3 shows a flow chart of a method 300 for predicting and/or detecting atrial fibrillation from R-R interval measurements and for predicting and/or detecting atrial fibrillation from raw heart rate signals. In a step 302, raw heart rate signals are obtained from, for example, an ECG of a user. In a step 304, R-R intervals are obtained from the obtained raw hearth signals. In a step 306, the obtained R-R interval is analyzed using one or more traditional heart rate variability measurements such as, for example, time domain measures, frequency domain measures, and non-linear heart rate variability. In a step 308, the obtained R-R interval is analyzed using one or more non-traditional heart rate variability measurements such as, for example, RR (n-i) for bigeminy and trigeminy detection, and the generation of a periodic autoregressive moving average (PARMA). In a step or more physiological parameter meets a pre-determined or learned threshold(s). Two or more of the physiological parameters may be combined to provide a trigger message. That is, a particular trigger message may be provided to the user if two or more pre-determined threshold(s) for the physiological parameter(s) are met.

Table 1 below shows an exemplary table of physiological parameters that may be measured (left column), features of interest to be measured or threshold types to be met (middle column), and exemplary trigger messages (right column).

TABLE 1

| Physiological Parameter | Measurements/Threshold | Sample Trigger Messages |
|---|---|---|
| Heart Rate | Heart Rate Variability (HRV), Non-linear Transformation of RR Intervals | Measure ECG; See Your Doctor |
| Heart Sound | Sound Features | Abnormal Heart Sound; Measure ECG; See Your Doctor |
| Blood Pressure | Upper and Lower Thresholds | High/Low Blood Pressure; Take BP Medication; Exercise; See Your Doctor |
| Blood Oxygenation | O2 Saturation, O2 Saturation Variability | High Risk of Hypoventilation; High Risk of Sleep Disorder such as Apnea; See Your Doctor |
| Blood Glucose | Upper and Lower Thresholds | High Risk of Hypoglycemia; See Your Doctor |
| Temperature | Temperature, Temperature Changes | Fever; Take OTC Fever Medication; See Your Doctor |
| Physical Activity (accelerometer data) | Gait, Chest Compressions, Speed, Distance | Monitor Senior or Infant Posture, e.g. if senior/infant has fallen |
| Electrocardiogram (ECG) | ECG Features (E.g. QT, QRS, PR intervals, HRV ,etc. | High Risk of Certain Cardiac Diseases; Sleep apnea; See Your Doctor |
| Breath Content (Breathalyzer data) | Percentage of the Certain Chemicals | High Risk of Certain Dental Disease, Diabetes, etc.; See Your Doctor |

310, features from the obtained heart rate features are analyzed using one or more of wavelet features and shape based features from a Hilbert transform. In a step 312, a feature selection occurs. In a step 314, a real time prediction or detection of atrial fibrillation, and/or in a step 316, the heart rate variability measurements may be labelled and saved for offline training of a machine learning algorithm or set of machine learning operations, and then may be subsequently used to make a real time prediction and/or detection of atrial fibrillation.

Although the above steps show methods 200 and 300 in accordance with many embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial to the user or subject.

One or more of the steps of method 200 and 300 may be performed with circuitry, for example, one or more of a processor or a logic circuitry such as a programmable array logic for a field programmable gate array. The circuitry may be programmed to provide one or more of the steps of methods 200 and 300, and the program may comprise program instructions stored on a non-transitory computer readable medium or memory or programmed steps of the logic circuitry such as the programmable array logic or the field programmable gate array, for example.

Aspects of the present disclosure provide systems and methods for monitoring one or more physiological parameters and providing a trigger message to the user if the one The machine learning based algorithms or operations as described herein may be used to determine the appropriate trigger thresholds in response to the raw physiological data input and/or user-input physiological parameters (e.g. age, height, weight, gender, etc.). Features of the raw physiological data input may be selected, extracted, labelled, clustered, and/or analyzed. These processed features may then be analyzed using one or more machine learning operation such as ranking the feature(s), classifying the feature(s), predicting the feature(s), and clustering the feature(s). The various machine learning algorithms described herein may be used to analyze the features to detect and predict health conditions and generate recommendations or user action items to improve the health of the user. For instance, the machine learning algorithms may be trained to identify atrial fibrillation or other conditions in response to the non-heart rate physiological parameter(s) such as age, gender, body mass index (BMI), activity level, diet, and others in combination with the raw heart rate data and HRV that can be extracted therefrom.

The systems and methods for monitoring one or more physiological parameters and providing a trigger message to the user if the one or more physiological parameter meets a pre-determined threshold(s) described herein may be implemented as software provided as a set of instructions on a non-transitory computer readable medium. A processor of a computing device (e.g. a tablet computer, a smartphone, a smart watch, a smart band, a wearable computing device, or the like) may execute this set of instructions to receive the input data and detect and/or predict atrial fibrillation therefrom. The software may be downloaded from an online application distribution platform such as the Apple iTunes or App Store, Google Play, Amazon App Store, and the like. The software may be loaded on and executed by the portable computing device of the user such as with the processor of the computing device. The software may also provide both the triggering application described herein and the heart rate monitoring and analysis for detecting atrial fibrillation or other heart conditions described herein.

In an embodiment, a method and system for longitudinal monitoring of a patient's or any consumer's (after referred to as "patient") health using various ECG monitoring devices is described herein. The ECG monitoring devices generate ECG signal data which can be stored in a database for further analysis. The ECG data, which can be stored in a database along with other patient information, can be analyzed by a processing device, such as a computer or server, using various algorithms.

Various ECG monitoring or recording devices, hereinafter referred to as ECG monitoring devices, can be used to record the ECG data. For example, the ECG monitoring device can be a handheld, portable, or wearable smartphone based device, as described in U.S. Pat. No. 8,301,232, which is herein incorporated by reference in its entirety for all purposes. A smartphone based device, or a device having wireless or cellular telecommunication capabilities, can transmit the ECG data to a database or server directly through the internet. These types of ECG monitoring devices as well as other ECG monitoring devices include portable devices, wearable recording devices, event recorders, and Holter monitors. Clinical or hospital based ECG recording devices can also be used and integrated into the system. Such devices may be able to transmit stored ECG data through a phone line or wirelessly through the internet or cellular network, or may need to be sent to a data collection center for data collection and processing. The ECG data can be tagged with the type of ECG monitoring device used to record the data by, for example, including it in metadata for indexing and searching purposes.

The ECG monitoring devices can be single lead devices or multiple lead devices, where each lead generally terminates with an electrode. Some embodiments may even be leadless and have electrodes that are integrated with the body or housing of the device, and therefore have a predetermined relationship with each other, such as a fixed spacing apart from each other. The orientation and positioning of the single lead in a single lead device or of each lead of the multiple lead device or of the electrodes of the leadless device can be transmitted with the ECG data. The lead and/or electrode placement may be predetermined and specified to the patient in instructions for using the device. For example, the patient may be instructed to position the leads and/or electrodes with references to one or more anatomical landmarks on the patient's torso. Any deviation from the predetermined lead and/or electrode placement can be notated by the patient or user when transmitting the ECG data. The lead and electrode placement may be imaged using a digital camera, which may be integrated with a smart phone, and transmitted with the ECG data and stored in the database. The lead and electrode placement may be marked on the patient's skin for imaging and for assisting subsequent placement of the leads and electrodes. The electrodes can be attached to the skin using conventional methods which may include adhesives and conducting gels, or the electrodes may simply be pressed into contact with the patient's skin. The lead and electrode placement may be changed after taking one recording or after recording for a predetermined or variable amount of time. The ECG data can be tagged with the numbers of leads and/or electrodes and the lead and/or electrode placement, including whether adhesives and/or conducting gels were used. Again, this information can be including in metadata for indexing and searching purposes.

The ECG signal data can be continuously recorded over a predetermined or variable length of time. Continuous ECG recording devices can record for up to 1, 2, 3, 4, 5, 6, 7, 8, 9, 10, 11, 12, 13, or 14 days. Alternatively or additionally, the ECG data can be recorded on demand by the patient at various discrete times, such as when the patient feels chest pains or experiences other unusual or abnormal feelings. The on demand ECG recorder can have a memory buffer that can record a predetermined amount of ECG data on a rolling basis, and when activated by the patient to record a potential event, a predetermined amount of ECG data can be saved and/or transmitted. The predetermined amount of ECG data can include a predetermined amount of ECG data before activation and a predetermined amount of ECG data after activation such that a window of ECG data is captured that encompasses the potential event. The time period between ECG recordings may be regular or irregular. For example, the time period may be once a day, once a week, once a month, or at some other predetermined interval. The ECG recordings may be taken at the same or different times of days, under similar or different circumstances, as described herein. One or more baseline ECGs can be recorded while the patient is free of symptoms. The baseline ECGs can be periodically recorded and predetermined intervals and/or on-demand. The same ECG recording device or different ECG recording devices may be used to record the various ECG of a particular patient. All this information may be tagged to or associated with the ECG data by, for example, including it in the metadata for indexing and searching purposes.

The ECG data can be time stamped and can be annotated by the patient or health care provider to describe the circumstances during which the ECG was recorded, preceding the ECG recording, and/or following the ECG recording. For example, the system and device can have an user interface for data entry that allows the patient to enter in notes regarding the conditions and circumstances surrounding the ECG recording. This additional data can be also included as metadata for indexing and searching purposes. For example, location, food, drink, medication and/or drug consumption, exercise, rest, sleep, feelings of stress, anxiety, pain or other unusual or abnormal feelings, or any other circumstance that may affect the patient's ECG signal can all be inputted into the device, smart phone, computer or other computing device to be transmitted to the server or database along with the ECG data. The annotated data can also include the patient's identity or unique identifier as well as various patient characteristics including age, sex, race, ethnicity, and relevant medical history. The annotated data can also be time stamped or tagged so that the ECG data can be matched or correlated with the activity or circumstance of interest. This also allows comparison of the ECG before, after and during the activity or circumstance so that the effect on the ECG can be determined.

The ECG data and the associated metadata can be transmitted from the device to a server and database for storage and analysis. The transmission can be real-time, at regular intervals such as hourly, daily, weekly and any interval in between, or can be on demand. The metadata facilitates the searching, organizing, analyzing and retrieving of ECG data. Comparison and analysis of a single patient's ECG data can be performed, and/or comparison of ECG data between patients can be performed. For example, the metadata can be used to identify and select a subset of ECG data where an activity or circumstance, such as the taking of medication, occurred within a predetermined amount of time to the ECG data. The components of the ECG signal data, such as the P wave, T wave, and QRS complex and the like, the amplitudes of the components, the ratios between the components, the width of the components, and the delay or time separation between the components, can be extracted, compared, analyzed, and stored as ECG features. For example, the P wave and heart rate can be extracted and analyzed to identify atrial fibrillation, where the absence of P waves and/or an irregular heart rate may indicate atrial fibrillation. The extracted ECG features can also be included in the metadata for indexing and searching.

The changes in the ECG signal over time in view of the activities and circumstances can be compared with changes over time and circumstances observed within a database of ECG's. Comparisons may include any comparison of data derived from any other ECG signal or any database of ECG's or any subset of ECG data, or with data derived from any database of ECG's. Changes in any feature of the ECG signal over time may be used for a relative comparison with similar changes in any ECG database or with data derived from an ECG database. The ECG data from the baseline ECG and the ECG data from a potential adverse event can be compared to determine the changes or deviations from baseline values. In addition, both the baseline ECG and the ECG data recorded from the patient can be compared to one or more predetermined template ECGs which can represent a normal healthy condition as well as various diseased conditions, such as myocardial infarction and arrhythmias.

The comparisons and analysis described herein can be used to draw conclusions and insights into the patient's health status, which includes potential health issues that the patient may be experiencing at the time of measurement or at future times. Conclusions and determinations may be predictive of future health conditions or diagnostic of conditions that the patient already has. The conclusions and determinations may also include insights into the effectiveness or risks associated with drugs or medications that the patient may be taking, have taken or may be contemplating taking in the future. In addition, the comparisons and analysis can be used to determine behaviors and activities that may reduce or increase risk of an adverse event. Based on the comparisons and analysis described herein, the ECG data can be classified according to a level of risk of being an adverse event. For example, the ECG data can be classified as normal, low risk, moderate risk, high risk, and/or abnormal. The normal and abnormal designation may require health care professional evaluation, diagnosis, and/or confirmation.

Diagnosis and determination of an abnormality, an adverse event, or a disease state by physicians and other health care professionals can be transmitted to the servers and database to be tagged with and associated with the corresponding ECG data. The diagnosis and determination may be based on analysis of ECG data or may be determined using other tests or examination procedures. Professional diagnosis and determinations can be extracted from the patient's electronic health records, can be entered into the system by the patient, or can be entered into the system by the medical professional. The conclusions and determinations of the system can be compared with actual diagnosis and determinations from medical professions to validate and/or refine the machine learning algorithms used by the system. The time of occurrence and duration of the abnormality, adverse event or disease state can also be included in the database, such that the ECG data corresponding with the occurrence and/or the ECG data preceding and/or following the abnormality, adverse event or disease state can be associated together and analyzed. The length of time preceding or following the abnormality may be predetermined and be up to 1 to 30 days, or greater than 1 to 12 months. Analysis of the time before the abnormality, adverse event or disease state may allow the system to identify patterns or correlations of various ECG features that precede the occurrence of the abnormality, adverse event or disease state, thereby providing advance detection or warning of the abnormality, adverse event or disease state. Analysis of the time following the abnormality, adverse event or disease state can provide information regarding the efficacy of treatments and/or provide the patient or physician information regarding disease progression, such as whether the patient's condition in improving, worsening or staying the same. The diagnosis and determination can also be used for indexing by, for example, including it in the metadata associated with the corresponding ECG data.

As described herein, various parameters may be included in the database along with the ECG data. These may include the patient's age, gender, weight, blood pressure, medications, behaviors, habits, activities, food consumption, drink consumption, drugs, medical history and other factors that may influence a patient's ECG signal. The additional parameters may or may not be used in the comparison of the changes in ECG signal over time and circumstances.

The conclusions, determinations, and/or insights into the patient's health generated by the system may be communicated to the patient directly or via the patient's caregiver (doctor or other healthcare professional). For example, the patient can be sent an email or text message that is automatically generated by the system. The email or text message can be a notification which directs the patient to log onto a secure site to retrieve the full conclusion, determination or insight, or the email or text message can include the conclusion, determination or insight. Alternatively or additionally, the email or text message can be sent to the patient's caregiver. The notification may also be provided via an application on a smartphone, tablet, laptop, desktop or other computing device.

As described herein, the system can identify behaviors, habits, activities, foods, drinks, medications, drugs, and the like which are associated with the patient's abnormal ECG readings. In addition to informing the patient of these associations, the system can provide instructions or recommendations to the patient to avoid these behaviors, habits, activities, foods, drinks, medications, drugs, and the like which are associated with the patient's abnormal ECG readings. Similarly, the system can identify behaviors, habits, activities, foods, drinks, medications, drugs, and the like which are associated with normal or improving ECG readings, and can instruct or recommend that the patient perform these behaviors, habits, and activities and/or consume these foods, drinks, medications, and drugs. The patient may avoid a future healthcare issue, as instructed or recommended by the system, by modifying their behavior, habits or by taking any course of action, including but not limited to taking a medication, drug or adhering to a diet or exercise program, which may be a predetermined course of action recommended by the system independent of any analysis of the ECG data, and/or may also result from insights learned through this system and method as described herein. In addition, the insights of the system may relate to general fitness and or mental wellbeing.

The ECG data and the associated metadata and other related data as described herein can be stored in a central database, a cloud database, or a combination of the two. The data can be indexed, searched, and/or sorted according to any of the features, parameters, or criteria described herein. The system can analyze the ECG data of a single patient, and it can also analyze the ECG data of a group of patients, which can be selected according to any of the features, parameters or criteria described herein. When analyzing data from a single patient, it may be desirable to reduce and/or correct for the intra-individual variability of the ECG data, so that comparison of one set of ECG data taken at one particular time with another set of ECG data taken at another time reveals differences resulting from changes in health status and not from changes in the type of ECG recording device used, changes in lead and electrode placement, changes in the condition of the skin (i.e. dry, sweaty, conductive gel applied or not applied), and the like. As described above, consistent lead and electrode placement can help reduce variability in the ECG readings. The system can also retrieve the patient's ECG data that were taken under similar circumstances and can analyze this subset of ECG data.

Figure 4:
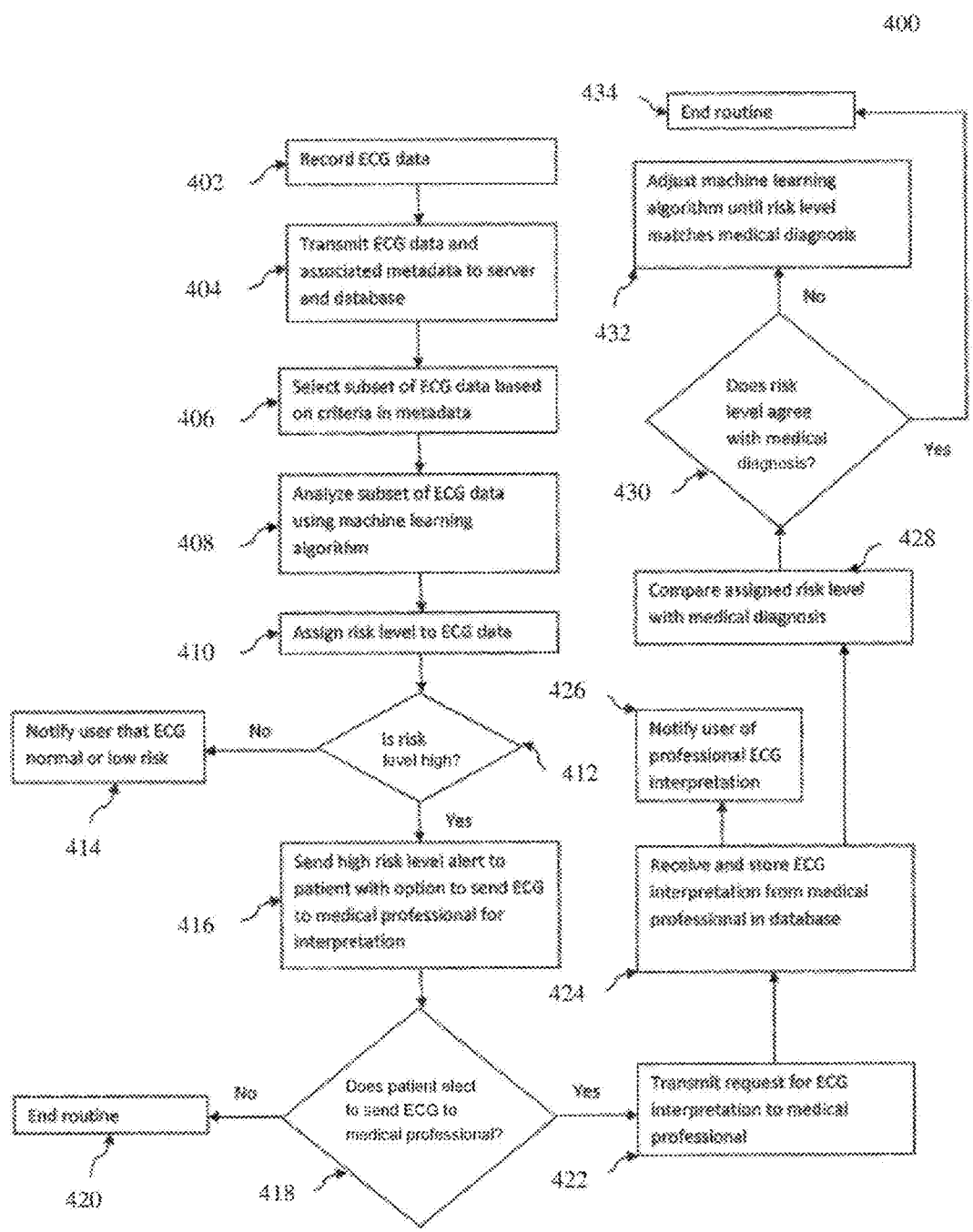
FIG. 4 shows an embodiment of the system and method of the ECG monitoring described herein.

FIG. 4 illustrates an embodiment of the system and method 400 of ECG monitoring described herein. The system can be implemented on a server or computer having a processor for executing the instructions described herein, which can be stored in memory. In step 402, ECG data can be recorded using any of the devices described herein for one or more patients. In step 404, the ECG data is transmitted along with associated metadata to a server and database that stores the ECG data. In step 406, a subset of the ECG data can be selected based on criteria in the metadata, such as user identity, time, device used to record the ECG data, and the like. In step 408, the subset of ECG data can be analyzed using a machine learning algorithm, which can assign a risk level to the ECG data in step 410. The system can then determine whether the risk level is high, as shown in step 412. If the risk level is low, the user can be notified that the ECG is normal or low risk, as shown in step 414. If the risk level is high, a high risk level alert can be sent to the patient with the option of sending the ECG to the medical professional for interpretation, as shown in step 416. The system then waits for the user's response to determine whether the patient elects to send the ECG to the medical professional for interpretation, as shown in step 418. If the patient does not wish to send the ECG to the medical professional for interpretation, the system can end the routine at this point, as shown in 420. If the patient does elect to send the ECG to the medical professional for interpretation, the request can be transmitted to the medical professional in step 422. The request to the medical professional can be sent to a workflow auction system as described in U.S. Provisional Application No. 61/800,879, filed Mar. 15, 2013, which is herein incorporated by reference in its entirety for all purposes. Once the medical professional has interpreted the ECG, the system can receive and store the ECG interpretation from the medical professional in the database, as shown in step 424. The system can then notify the user of the professional ECG interpretation, which can be sent to or accessed by the user, as shown in step 426. Additionally, the system can compare the assigned risk level with the medical diagnosis in step 428 and can determine whether the risk level determined by the system agrees with the medical diagnosis in step 430. If the risk level does not agree with the medical diagnosis, the machine learning algorithm can be adjusted until the risk level matches the medical diagnosis, as shown in step 432. If the risk level does agree with the medical diagnosis, the routine can be ended as shown in step 434.

Although the above steps show a method 400 in accordance with many embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial to the user or subject.

One or more of the steps of a method 400 may be performed with circuitry, for example, one or more of a processor or a logic circuitry such as a programmable array logic for a field programmable gate array. The circuitry may be programmed to provide one or more of the steps of a method 400, and the program may comprise program instructions stored on a non-transitory computer readable medium or memory or programmed steps of the logic circuitry such as the programmable array logic or the field programmable gate array, for example.

Aspects of the present disclosure provide systems and methods for generating a heart health score in response to continuously measured or monitored physiological parameter(s). The score may be given a quantitative value such as be graded from A to F or 0 to 100 for example (e.g. a great score may be an A or 100, a good score may be a B or 75, a moderate score may be a C or 50, a poor score may be a D or 25, and a failing score may be an F or 0.) If an arrhythmia is detected, the score may be below 50 for example. Other scoring ranges such as A to Z, 1 to 5, 1 to 10, 1 to 1000, etc. may also be used. Arrhythmia may be detecting using the machine learning based operations or algorithms described herein.

Figure 5:
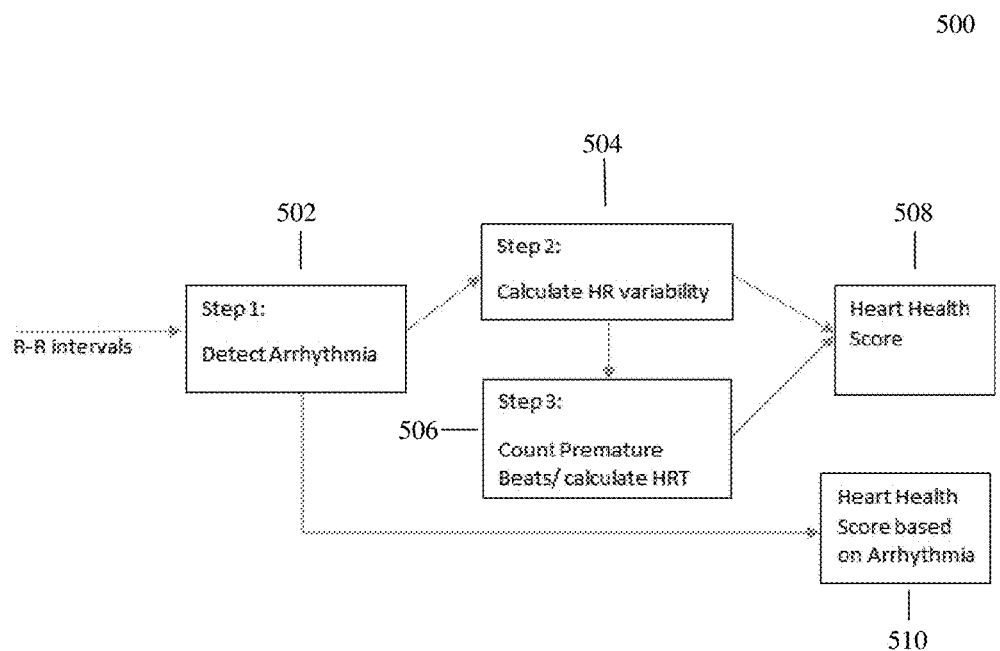
FIG. 5 shows a flow chart of an exemplary method to generate a heart health score in accordance with many embodiments.

FIG. 5 shows a flow chart of an exemplary method 500 to generate a heart health score in accordance with many embodiments.

In a step 502, an arrhythmia is detected. If an arrhythmia is detected (e.g. using the methods and/or algorithms disclosed herein), then the heart health score generated will be below 50. Depending on the severity of the arrhythmia detected, the heart score may be calculated or assigned within the ranges according to the table below in Table 2.

TABLE 2

| Arrhythmia | Heart Health score |
| --- | --- |
| ATRIAL FIBRILLATION, HR below 100 | 30-45 |
| ATRIAL FIBRILLATION, HR above 100 | 15-30 |
| Sinus Tachycardia | 20-40 |
| Supraventricular Tachycardia | 20-40 |
| Bradycardia | 20-40 |
| Bigeminy, Trigeminy | 30-50 |
| Short runs of High Heart Rate (VTACH suspect) | 10-30 |

In a step 504 a Heart Rate Variability (HRV) is calculated. HRV can be an indicator of heart health. The value for HRV value for a healthy heart is typically higher than HRV for an unhealthy heart. Also, HRV typically declines with age and may be affected by other factors, like stress, lack of physical activity, etc. HRV may be measured and analyzed using the methods described above. HRV may be calculated in the absence of arrhythmia, which may improve the accuracy of the HRV measurement. HRV may be determined and further analyzed as described above.

In a step 506, premature beats are counted and Heart Rate Turbulence (HRT) is calculated. Premature beats in the sequence of R-R intervals may be detected. Also, R-R intervals typically tend to recover at a certain pace after a premature beat. Using these two parameters (prematurity and pace of R-R recovery), HRT parameters may be calculated. There may be known deviations of HRT parameters associated with patients with risk of Congestive Heart Failure (CHF). These deviations, however, may be used to estimate an inverse measure. The number of premature beats per day (or per hour) may also be used as a measure of heart health. A low number of premature beats may indicate better heart health. In summary, the heart health score may be generated by combining at least heart rate variability (HRV), the number of premature beats, and heart rate turbulence (HRT). This combination (in the absence of arrhythmia) may provide an accurate estimate of how healthy the heart of the user is.

In a step 508, a heart health score is generated, and in a step 510, a hearth health score is generated based on an arrhythmia. To initially generate the score, a few hours (e.g. 2-5 hours) of measured R-R intervals may be required. A more accurate score may be generated after a week of continuous R-R interval measurements. Longer data sets may be required to detect significant arrhythmias as they may usually be detected within the first 7-8 days of monitoring.

Although the above steps show a method 500 in accordance with many embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial to the user or subject.

One or more of the steps of a method 500 may be performed with circuitry, for example, one or more of a processor or a logic circuitry such as a programmable array logic for a field programmable gate array. The circuitry may be programmed to provide one or more of the steps of a method 500, and the program may comprise program instructions stored on a non-transitory computer readable medium or memory or programmed steps of the logic circuitry such as the programmable array logic or the field programmable gate array, for example.

Figure 6:
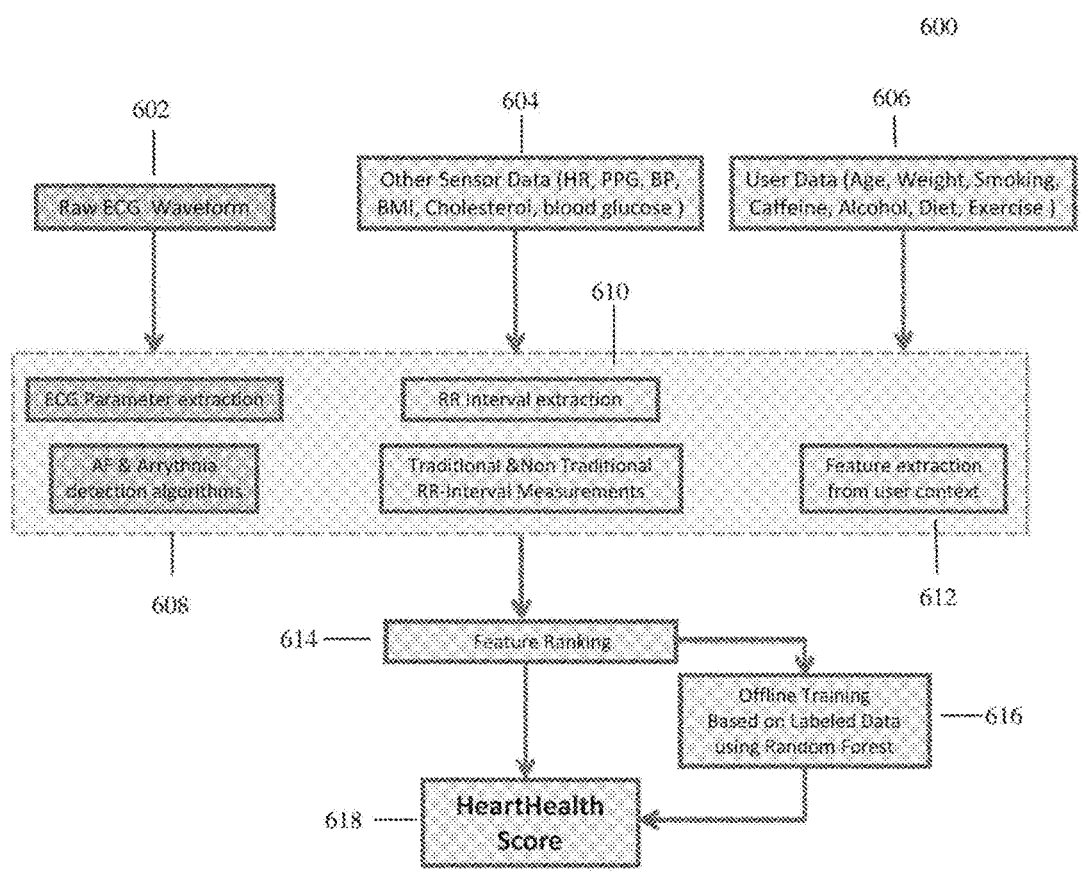
FIG. 6 shows an exemplary method of generating a heart score.

FIG. 6 shows a further method 600 of generating a heart score. In addition to the parameters which may be derived from the heart rate data described above, the heart health score may also be generated in response to further physiological parameters as shown in FIG. 6.

In a step 602, a raw ECG waveform is obtained. In a step 608, ECG parameters are extracted from the raw ECG waveform data and arrhythmia prediction and/or detection algorithms are run to analyze the obtained raw ECG waveform data.

In a step 604, physiological parameters may be measured using a sensor of the user's local computing device or an accessory thereof. Such measured physiological parameters may include blood pressure, user activity and exercise level, blood oxygenation levels, blood sugar levels, an electrocardiogram, skin hydration or the like of the user. These physiological parameters may be measured over time such as over substantially the same time scale or length as the measurement of heart rate. In a step 610, an R-R interval is extracted and both traditional and non-traditional heart rate measures are used to analyze the measured heart rate and physiological parameters.

In a step 606, additional physiological parameters for determining the heart health score may be input by the user. These parameters may include the age, the gender, the weight, the height, the body type, the body mass index (BMI), the personal medical history, the family medical history, the exercise and activity level, the diet, the hydration level, the amount of sleep, the cholesterol level, the alcohol intake level, the caffeine intake level, the smoking status, and the like of the user. For example, the heart health score may be weighted by age and/or gender to provide the user an accurate assessment of his or her heart health in response to the heart rate data. In a step 612, feature extraction is used to analyze the inputted physiological parameters.

In a step 614 feature ranking and/or feature selection occurs. In a step 618, a real time prediction or detection of atrial fibrillation, and/or in a step 616, the heart rate variability measurements may be labelled and saved for offline training of a machine learning algorithm or set of machine learning operations, and then may be subsequently used to make a real time prediction and/or detection of atrial fibrillation. A plurality of heart health scores may be generated by a plurality of users to generate a set of population data. This population data may be used to train the machine learning algorithms described herein such that the trained algorithm may be able to detect and predict atrial fibrillation or other health conditions from user data.

Although the above steps show a method 600 in accordance with many embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial to the user or subject.

One or more of the steps of a method 600 may be performed with circuitry, for example, one or more of a processor or a logic circuitry such as a programmable array logic for a field programmable gate array. The circuitry may be programmed to provide one or more of the steps of a method 600, and the program may comprise program instructions stored on a non-transitory computer readable medium or memory or programmed steps of the logic circuitry such as the programmable array logic or the field programmable gate array, for example.

The systems and methods for generating a heart health score in response to continuously measured or monitored physiological parameter(s) may comprise a processor of a computing device and software. A processor of a computing device (e.g. a tablet computer, a smartphone, a smart watch, a smart band, a wearable computing device, or the like) may execute this set of instructions to receive the input data and detect and/or predict atrial fibrillation therefrom. The software may be downloaded from an online application distribution platform such as the Apple iTunes or App Store, Google Play, Amazon App Store, and the like. A display of the computing device may notify the user of the calculated heart health score and/or if further measurements are required (e.g. to perform a more accurate analysis).

Figure 7:
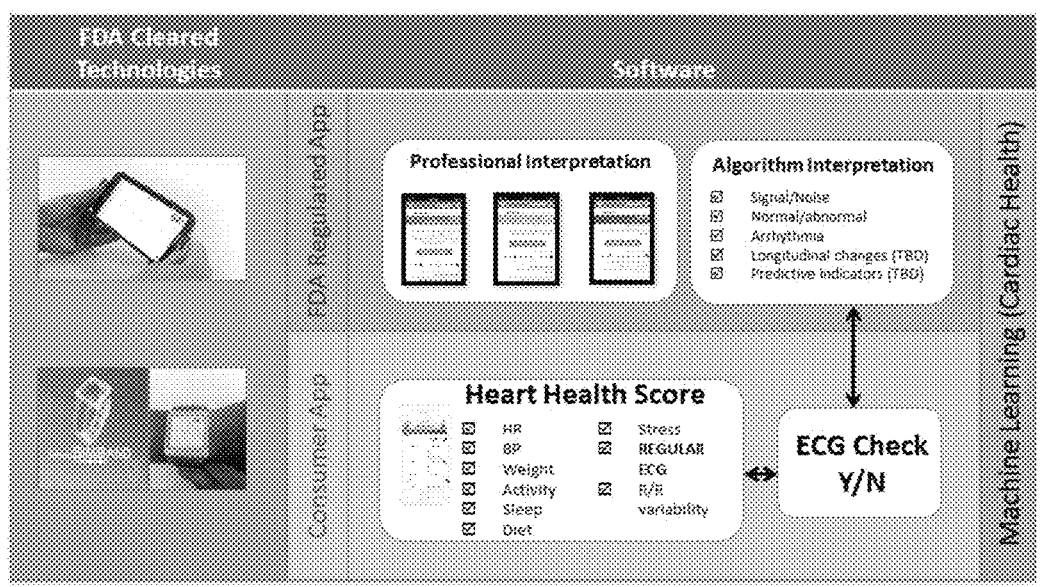
FIG. 7 shows a schematic diagram of the executed application described herein.

FIG. 7 shows a schematic diagram of the executed application described herein. The heart health score may be provided on a software application such as a mobile app downloaded from an application distribution platform and executed on a local computing device of the user as described above. This executed application may instruct the user to take active steps in response to a poor or moderate heart health score. For example, the instructions to the user may be to make a corrective measure such as to modify his or her diet, exercise pattern, sleep pattern, or the like.

Alternatively or in combination, the instructions to the user may be to take a further step such as to take an electrocardiogram (e.g. to verify the presence of an arrhythmia), enroll in an electrocardiogram over-read service, or schedule an appointment with a physician or other medical specialist. If the heart health score is below a desired threshold for good heart health, the executed application may link the user to a second execute application with further application features. Alternatively or in combination, these further features may be unlocked on the first executed application if the heart health score is below the threshold. In at least some cases, a prescription or verification from a medical professional may also be required to unlock the further application features.

Figure 8:
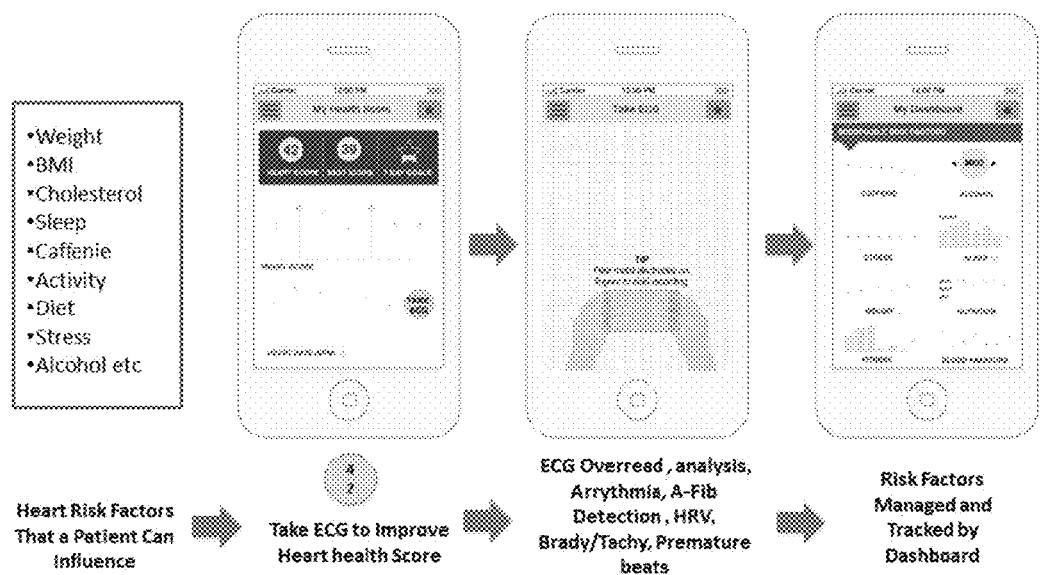
FIG. 8 shows exemplary screenshots of the executed application.

FIG. 8 shows screenshots of the executed application. The further features unlocked may include the ability to read electrocardiogram (ECG) data from a sensor coupled to the local computing device and display the electrocardiogram (ECG) in real-time and/or detect and alert for atrial fibrillation based on the electrocardiogram (ECG) in real-time (e.g. as described in U.S. application Ser. Nos. 12/796,188, 13/108,738, 13/420,540, and 13/964,490). As shown in FIG. 8, these further features may include an electrocardiogram (ECG) over-read service such as that described in U.S. application Ser. No. 14/217,032. The first executed application may comprise a consumer software application and the second executed application may comprise a medical professional or regulated software application or set of features of the first executed application. As described herein and shown in FIG. 8, the executed application may provide a dash board to track the heart health of the user and show risk factors which may be monitored and tracked by the user. The dash board may be provided with further features such as that described in U.S. Ser. No. 61/915,113 (filed Dec. 12, 2013).

Figure 9:
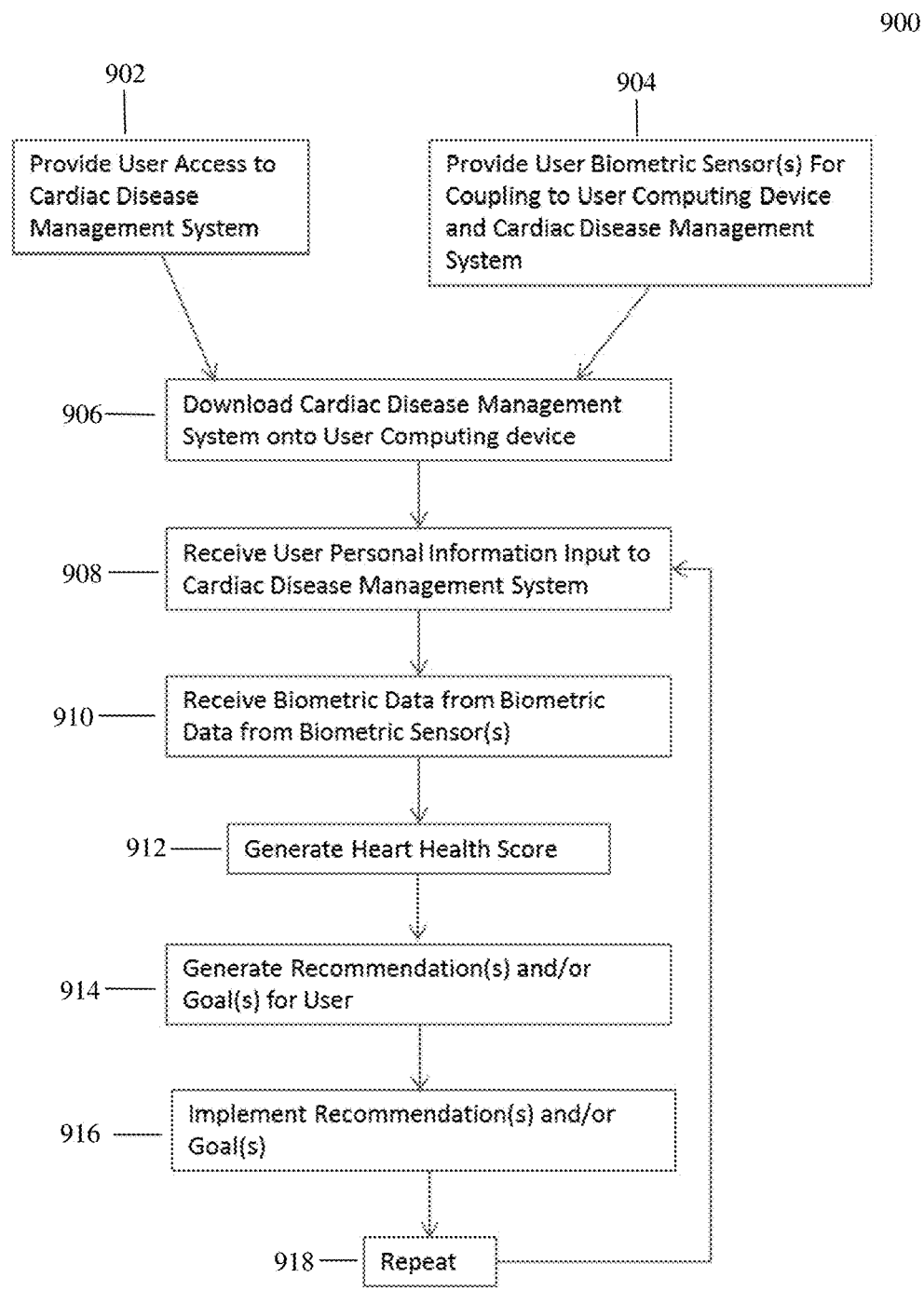
FIG. 9 shows an exemplary method for cardiac disease and rhythm management.

FIG. 9 shows a method 900 for cardiac disease and rhythm management, which may, for example, be implemented with the system 100 described herein. In a step 902, a user or subject is provided access to a cardiac disease and/or rhythm management system such as system 100. Step 902 may comprise prescribing the use of the system 100 for the user or subject. In a step 904, the user or subject is provided one or more biometric sensors. These biometric sensor(s) may couple to a computing device of the user or subject, e.g. a personal desktop computer, a laptop computer, a tablet computer, a smartphone, etc., and associated software loaded thereon.

In a step 906, the user or subject downloads the cardiac disease and/or rhythm management system software onto their computing device. For example, the system software may comprise a mobile software application ("mobile app") downloaded from the Apple App Store, Google Play, Amazon Appstore, BlackBerry World, Nokia Store, Windows Store, Windows Phone Store, Samsung Apps Store, and the like. The downloaded system software, e.g. mobile app 101a, may be configured to interface with the biometric sensors provided to the user or subject in the step 154.

In a step 908, personal information input to the cardiac disease management system is received. For example, the user or subject may enter his or her gender, height, weight, diet, disease risk factors, etc. into the mobile app 101a. Alternatively or in combination, this personal information may be input on behalf of the user or subject, for example, by a physician of the user or subject.

In a step 910, biometric data is received from the biometric sensors provided to the user or subject. For example, the system 100 and the mobile app 101a may receive ECG data and heart rate from handheld sensor 103, activity data from wrist-worn activity sensor 105, blood pressure and heart rate data from mobile blood pressure monitor 107a, and other data such as weight and body fat percentage data from a "smart" scale in communication with the local computing device 101.

In a step 912, a cardiac health score is generated. The cardiac health score can be generated by considering and weighing one or more influencing factors including the incidence of atrial fibrillation or arrhythmia as detected by the handheld ECG monitor, the heart rate of the user or subject, the activity of the user or subject, hours of sleep and rest of the user or subject, blood pressure of the user or subject, etc. Often, the incidence of atrial fibrillation or arrhythmia will be weighed the most. The cardiac health score may be generated by a physician or a machine learning algorithm provided by the remote server or cloud-based service 113, for example. A plurality of users and subject may concurrently use the cardiac health and/or rhythm management system 100 and the machine learning algorithm may, for example, consider population data and trends to generate an individual user or subject's cardiac health score.

In a step 914, one or more recommendations or goals is generated for the user or subject based on or in response to the generated cardiac health score. These recommendation(s) and/or goal(s) may be generated automatically based on or in response to the biometric and personal information of the user or subject. For example, the machine learning algorithm may generate these recommendation(s)/goal(s). Alternatively or in combination, a physician or other medical specialist may generate the recommendation(s) and/or goal(s), for example, based on or in response to the biometric and personal information of the user or subject. The physician or other medical professional may access the patient data through the Internet as described above.

In a step 916, the patient implements many if not all of the recommendation(s) and/or goal(s) provided to him or her. And in a step 916, steps 908 to 916 may be repeated such that the user or subject may iteratively improve their cardiac health score and their overall health.

Although the above steps show method 900 of managing cardiac disease and/or rhythm in accordance with many embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial to the user or subject.

One or more of the steps of the method 900 may be performed with circuitry, for example, one or more of a processor or a logic circuitry such as a programmable array logic for a field programmable gate array. The circuitry may be programmed to provide one or more of the steps of the method 900, and the program may comprise program instructions stored on a non-transitory computer readable medium or memory or programmed steps of the logic circuitry such as the programmable array logic or the field programmable gate array, for example.

In some embodiments, the heart rate information (or an extracted portion of HR information) may be used to compare to a database of similar information that has been correlated with cardiac events. For example, heart rate information may be compared to a database of HR information extracted for ECG recordings of patients known to be experiencing cardiac problems. Thus, patterns of heart rate information taken from a subject may be compared to patterns of cardiac information in a database. If there is a match (or a match within a reasonable closeness of fit), the patient may be instructed to record an ECG, e.g. using an ambulatory ECG monitor. This may then provide a more detailed view of the heart. This method may be particularly useful, as it may allow recording and/or transmission and/or analysis of detailed electrical information about the heart at or near the time (or shortly thereafter) when a clinically significant cardiac event is occurring. Thus, the continuous monitoring may allow a subject to be alerted immediately upon an indication of the potential problem (e.g. an increase in HRV suggestive of a cardiac dysfunction). This may allow the coupling of continuous HR monitoring with ECG recording and analysis for disease diagnosis and disease management.

Figure 10:
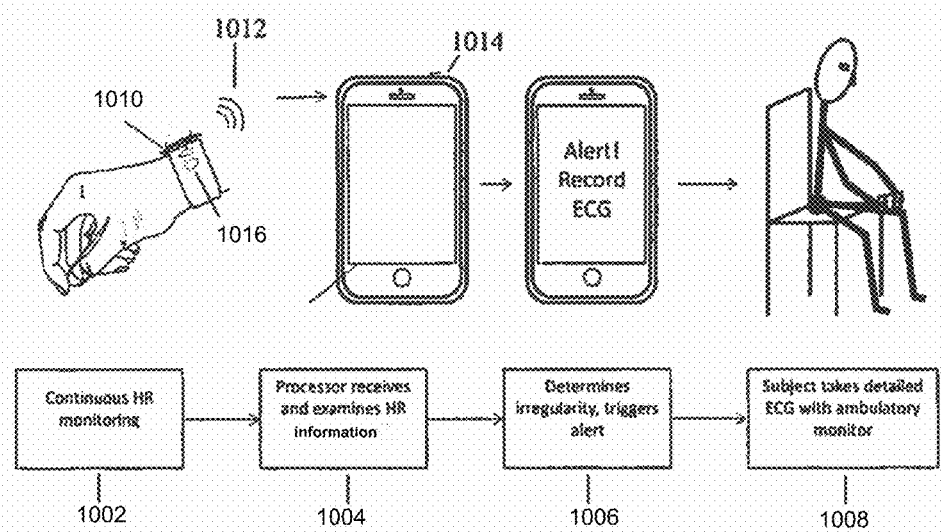
FIG. 10 shows an exemplary method for monitoring a subject to determine when to record an electrocardiogram (ECG)

FIG. 10 illustrates one variation of a method for monitoring a subject to determine when to record an electrocardiogram (ECG). In FIG. 10, a subject is wearing a continuous heart rate monitor (configured as a watch 1010, including electrodes 1016), shown in step 1002. The heart rate monitor transmits (wirelessly 1012) heart rate information that is received by the smartphone 1018, as shown in step 1004. The smartphone includes a processor that may analyze the heart rate information 1004, and when an irregularity is determined, may indicate 1006 to the subject that an ECG should be recorded. In FIG. 10, an ambulatory ECG monitor 1014 is attached (as a case having electrodes) to the phone 1018. The user may apply the ECG monitor as to their body (e.g. chest, between arms, etc.) 1008 to record ECGs that can then be saved and/or transmitted for analysis.

Figure 11:
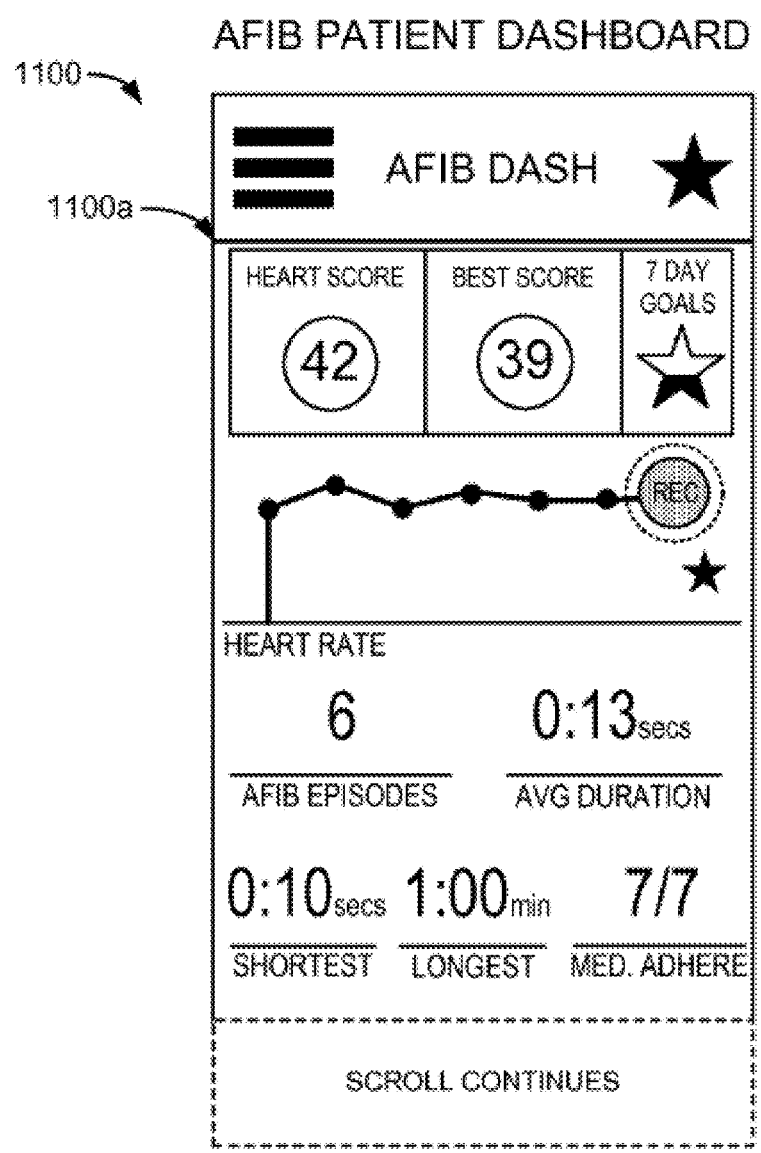
FIG. 11 shows an exemplary screenshot of a first aspect of a dashboard application.
Figure 11A:
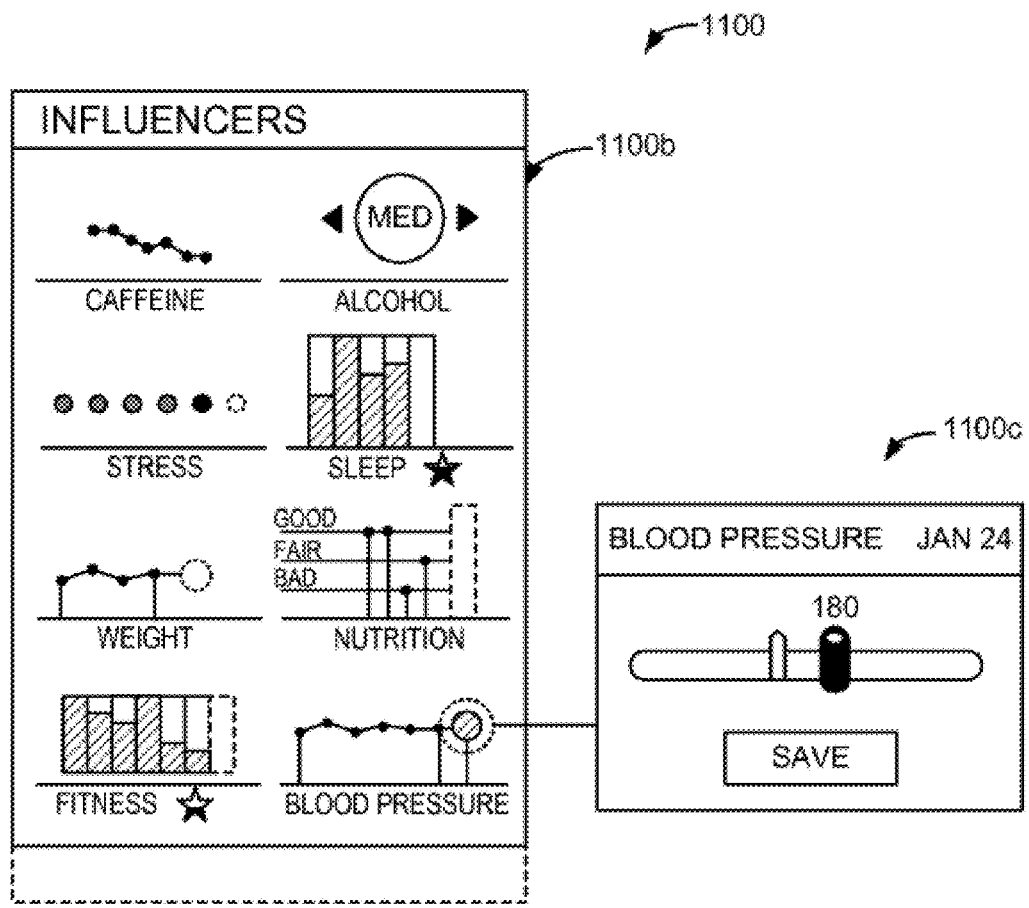
FIG. 11A shows an exemplary screenshot of a second aspect of a dashboard application.

FIGS. 11 and 11A show screenshots of an atrial fibrillation dashboard 1100 of a user interface for the cardiac disease and/or rhythm management system 100. FIG. 11 shows a top portion 1100a of the atrial fibrillation dashboard 1100 while FIG. 10A shows a bottom portion 1100b of the atrial fibrillation dashboard 1100.

The top portion 1100a of the atrial fibrillation dashboard 1100 as shown in FIG. 10 may display the current cardiac health score of the user or subject, a recent best cardiac health score of the user or subject, and a completion percentage of recommendation(s) and/or goal(s) for the user or subject. The user or subject may tap any one of the cardiac health score displays or the recommendation(s) and/or goal(s) displays to access more detailed information regarding the calculated health score(s) or recommendation(s) and/or goal(s), respectively. The top portion 1100a may also show an ECG of the user or subject and a button which may be tapped to record the ECG of the user or subject for the day. As discussed with reference to FIG. 1, the ECG may be recorded with a handheld sensor 103 in communication with the local computing device 100. The top portion 1000a may also show the number of atrial fibrillation episodes and the average duration of these atrial fibrillation episodes. This number and duration may be generated automatically by software or logic of the mobile app 101a based on or in response to the ECG measurements taken by the user or subject. Alternatively or in combination, a physician may access the atrial fibrillation dashboard 1100 of an individual user or subject, evaluate his or her ECGs, and provide the number of atrial fibrillation episodes and their duration to the mobile app 101a or other software loaded on the local computing device 101 of the user or subject. The shortest and longest durations of the atrial fibrillation episodes may also be shown by the top portion 1100a as well as the user or subject's daily adherence to a medication regime.

The bottom portion 1100b of the atrial fibrillation dashboard 1100 as shown in FIG. 10A may display one or more influencers which influence how the cardiac health score is generated. These influencers may include, for example, caffeine intake, alcohol intake, stress levels, sleep levels, weight, nutrition, fitness and activity levels, and blood pressure. Data for these influencers may be input automatically by one or more biometric sensors coupled to the local computing device 101 and/or the mobile app 101a. Alternatively or in combination, the data for these influencers may be input manually by the user or subject by tapping on the respective influencer display. For example, tapping on the blood pressure display area may cause a slider input 1100c for blood pressure to pop up. The user or subject may use the slider to enter and save his or her blood pressure for the day. Similar pop-ups or user-selected inputs may be provided for the other influencers. For example, the user or subject may enter his or her daily caffeine or alcohol intake, stress and sleep levels, nutrition levels, or activity and fitness levels (e.g. low/bad, medium/so-so, or high/good based on the user's age, gender, height, weight, etc. as can be indicated by an instruction page of the mobile app 101a). The influencer displays may also show the goal progression of the user or subject.

Figure 12:
FIG. 12 shows an exemplary screenshot of a first aspect of a goals and recommendations page of the cardiac disease and rhythm management system interface or mobile app.
Figure 12A:
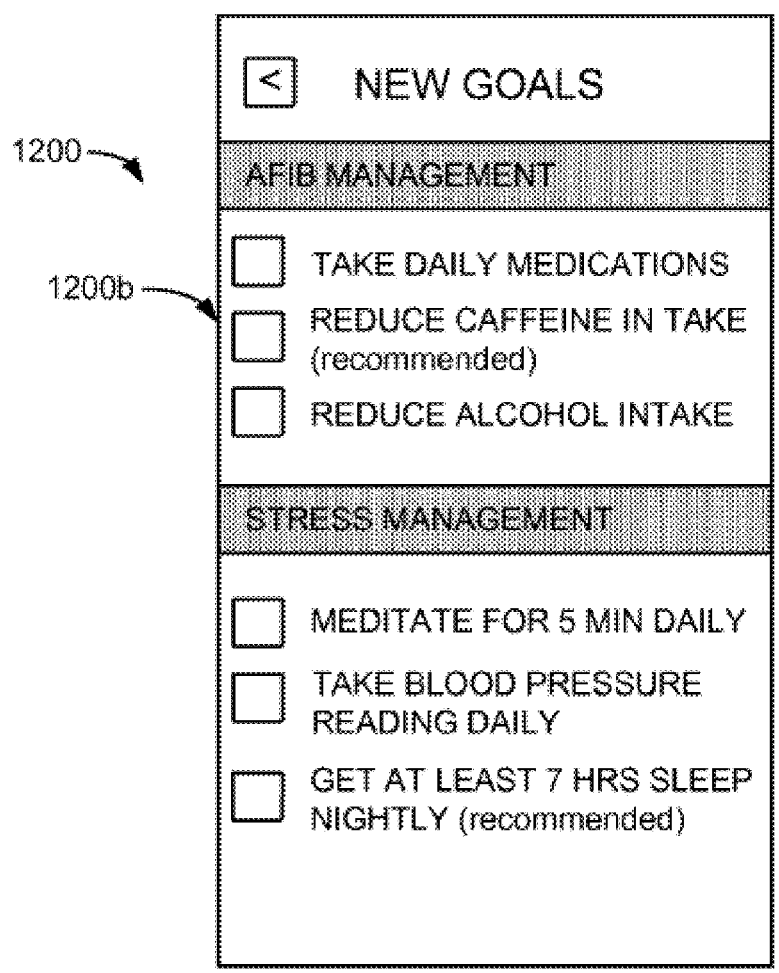
FIG. 12A shows an exemplary screenshot of a second aspect of a goals and recommendations page of the cardiac disease and rhythm management system interface or mobile app.

FIGS. 12 and 12A show screenshots of a goals and recommendations page 1200 of the cardiac disease and rhythm management system interface or mobile app 101a. A top portion 1200a of the goals and recommendations page 1100 may comprise a listing of 7-day goals for the user or subject. The top portion 1200a may further comprise everyday goals for the user or subject which often cannot be removed or changed. The user or subject can check off these goals or recommendations as he or she meets them. The top portion 1200a may track goal completion percentage over a 7-day period. The user or subject can set the same goals for the next day and/or set new goals.

A bottom portion 1200b of the goals and recommendations page 1200 may comprise a listing of new goals which the user or subject may add. The new goals may be categorized into goals or recommendations for atrial fibrillation management, stress management, and/or other categories. For example, goals for atrial fibrillation management may include taking daily medications, reducing caffeine intake, and reducing alcohol intake. And, goals for stress management may include meditate for 5 minutes daily, take blood pressure reading daily, and getting at least 7 hours of sleep nightly. Using the goals and recommendations page 1200, the user or subject can set their goals for the week. One or more of these goals may be automatically recommended to the user or subject or be recommended by a physician having access to the dashboard 1100. For example, goals may be recommended based on last week's progress. The completion of recommended goals can result in the user or subject earning more "points," in effect gamifying health and cardiac rhythm management for the user or subject. Alternatively or in combination, the goals may be set by a physician having access to the dashboard 1100.

Figure 13:
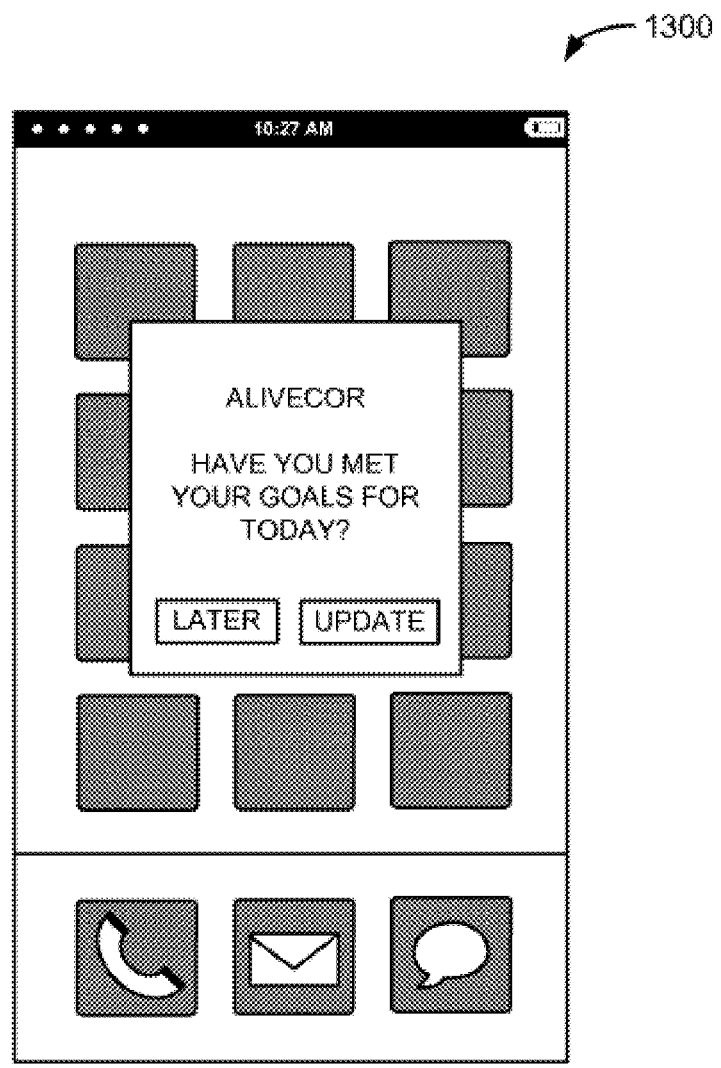
FIG. 13 shows an exemplary screenshot of a user's local computing device notifying the user with a pop-up notice to meet their daily recommendations and goals.

FIG. 13 shows a screenshot of a user's local computing device notifying the user with a pop-up notice 1300 to meet their daily recommendations and goals. By tapping on the pop-up notice, 1300, the user or subject can be taken to the atrial fibrillation dashboard where the user or subject can update or otherwise manage their cardiac health.

Figure 14:
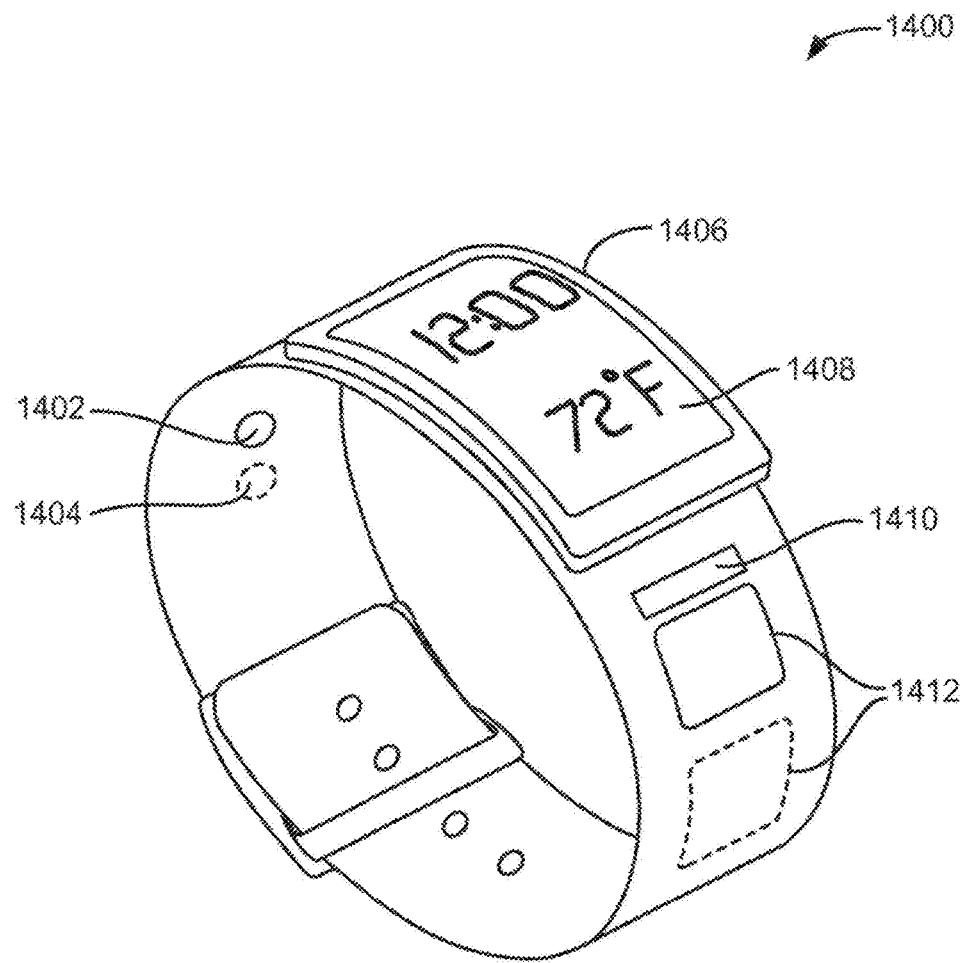
FIG. 14 shows an embodiment comprising a smart watch which includes at least one heart rate monitor and at least one activity monitor.

FIG. 14 shows an embodiment comprising a smart watch 1400 which includes at least one heart rate monitor 1402 and at least one activity monitor 1404. One or more processors are coupled to one or more non-transitory memories of the smart watch and configured to communicate with the heart rate monitor 1402 and the activity monitor 1404. The one or more processors are further coupled to an output device 1408. Processor executable code is stored on the one or more memories and when executed by the one or more processors causes the one or more processors to determine if heart rate and activity measurements represent an advisory condition for recording an ECG, and generate and send notification signals through the output device 1408 when an advisory condition for recording an ECG is determined.

For example, presently available smart watches include motion sensors such as pedometers. Pedometers can be based on an accelerometer or electromechanical mechanism such as a pendulum, magnetic reed proximity switch, and a spring suspended lever arm with metal-on-metal contact. Modern accelerometers are often small micro electro-mechanical systems and are well known by those skilled in the art. Heart rate monitors are readily available with smart phones as well as smart watches. One type uses an optical sensor to detect the fluctuation of blood flow. The signal can be amplified further using, for example, a microcontroller to count the rate of fluctuation, which is actually the heart rate.

An advisory condition for recording an ECG may occur due to, for example, large continuing fluctuations in heart rate. An advisory condition for recording an ECG can also occur when a measured heart rate increases rapidly without a corresponding increase in activity monitored by, for example, an accelerometer. By comparing measured heart rate changes with measured activity changes, the presently disclosed software or "app" minimizes false alarms are minimized. ECG devices are described in U.S. Ser. No. 12/796,188, filed Jun. 8, 2010, now U.S. Pat. No. 8,509,882, hereby expressly incorporated herein by reference in its entirety. The ECG device can be present in a smart watch band or a smart phone. In one embodiment, the ECG device includes an electrode assembly configured to sense heart-related signals upon contact with a user's skin, and to convert the sensed heart-related signals to an ECG electric signal. The ECG device transmits an ultrasonic frequency modulated ECG signal to a computing device such as, for example, a smartphone. Software running on the computing device or smartphone digitizes and processes the audio in real-time, where the frequency modulated ECG signal is demodulated. The ECG can be further processed using algorithms to calculate heart rate and identify arrhythmias. The ECG, heart rate, and rhythm information can be displayed on the computer or smartphone, stored locally for later retrieval, and/or transmitted in real-time to a web server via a 2G/3G/4G, WiFi or other Internet connection. In addition to the display and local processing of the ECG data, the computer or smartphone can transmit, in real-time, the ECG, heart rate and rhythm data via a secure web connection for viewing, storage and further analysis via a web browser interface.

In another embodiment, the converter assembly of an ECG device is integrated with, and electrically connected to the electrode assembly and is configured to convert the electric ECG signal generated by electrode assembly to a frequency modulated ECG ultrasonic signal having a carrier frequency in the range of from about 18 kHz to about 24 kHz. It is sometimes desirable to utilize a carrier frequency in the 20 kHz to 24 kHz range. The ultrasonic range creates both a lower noise and a silent communication between the acquisition electronics and the computing device such as the smartphone, notebook, smart watch and the like.

A kit can include downloadable software such as an "app" for detecting an advisory condition for recording an ECG and an ECG device. The ECG device can be present on a watch band for replacing a specific band on a smart watch. The ECG device can also be provided on a smart phone back plate for replacing an existing removable smartphone back. In another configuration, the ECG device is usable as a smartphone protective case.

Software on the smartphone or smart watch can also combine data and signals from other sensors built into the smartphone or smart watch such as a GPS.

While preferred embodiments of the present disclosure have been shown and described herein, it will be obvious to those skilled in the art that such embodiments are provided by way of example only. Numerous variations, changes, and substitutions will now occur to those skilled in the art without departing from the subject matter described herein. It should be understood that various alternatives to the embodiments of the subject matter described herein may be employed in practicing the subject matter described herein. It is intended that the following claims define the scope of the disclosure and that methods and structures within the scope of these claims and their equivalents be covered thereby.

What is claimed is:

1. A method of determining a presence of an arrhythmia of a first user, said method comprising:
   sensing a heart rate of said first user with a heart rate sensor coupled to said first user;
   transmitting said heart rate of said first user to a mobile computing device, wherein said mobile computing device is configured to sense an electrocardiogram;
   determining, using said mobile computing device, a heart rate variability of said first user based on said transmitted heart rate of said first user; and
   alerting said first user to sense an electrocardiogram of said first user, using said mobile computing device, in response to an irregularity in said heart rate variability.

2. The method of claim 1, wherein said heart rate sensor comprises one or more of a patch, a wristband, and an armband.

3. The method of claim 1, further comprising receiving biometric data of said first user from a biometric data sensor coupled to said first user.

4. The method claim 3, wherein said biometric data comprises one or more of a temperature of said first user, a blood pressure of said first user, and inertial data of said first user.

5. The method of claim 1, further comprising sensing an activity level of said first user with a motion sensor and comparing, using said mobile computing device, said heart rate variability of said first user to said activity level.

6. The method of claim 5, wherein said mobile computing device comprises a smartphone.

7. The method of claim 5, wherein said mobile computing device comprises a smartwatch.

8. The method of claim 1, further comprises determining a presence of said arrhythmia using a machine learning algorithm.

9. The method of claim 8, wherein said machine learning algorithm stores heart rate and heart rate variability data previously associated with arrhythmias in said first user and determines said presence of said arrhythmia based on said stored heart and heart rate variability data.

10. The method of claim 8, wherein said machine learning algorithm stores heart rate and heart rate variability data associated with arrhythmias in a second user and determines said presence of said arrhythmia in said first user based on said stored heart and heart rate variability data associated with arrhythmias in said second user.

11. A system for determining the presence of an arrhythmia of a first user, comprising a heart rate sensor coupled to said first user;
- a mobile computing device comprising a processor, wherein said mobile computing device is coupled to said heart rate sensor, and wherein said mobile computing device is configured to sense an electrocardiogram of said first user;
- a non-transitory computer readable medium encoded with a computer program including instructions executable by said processor to cause said processor to receive a heart rate of said first user from said heart rate sensor, determine a heart rate variability of said first user based on said heart rate of said first user, and alert said first user to record an electrocardiogram using said mobile computing device.

12. The system of claim 11, wherein said heart rate sensor comprises one or more of a patch, a wristband, and an armband.

13. The system of claim 11, wherein said system further comprises a biometric data sensor, and wherein said computer program including instructions executable by said processor further causes said processor to sense biometric data of said first user from said biometric data sensor.

14. The system claim 13, wherein said biometric data comprises one or more of a temperature of said first user, a blood pressure of said first user, and inertial data of said first user.

15. The system of claim 11, wherein said system further comprises a motion sensor, and wherein said computer program including instructions executable by said processor further causes said processor to sense an activity level of said first user from said motion sensor and compare said activity level to said heart rate variability of said first user.

16. The system of claim 15, wherein said mobile computing device comprises a smartphone.

17. The system of claim 15, wherein said mobile computing device comprises a smartwatch.

18. The system of claim 11, further comprises determining a presence of said arrhythmia using a machine learning algorithm.

19. The system of claim 18, wherein said machine learning algorithm stores heart rate and heart rate variability data previously associated with arrhythmias in said first user and determines said presence of said arrhythmia based on said stored heart and heart rate variability data.

20. The system of claim 19, wherein said machine learning algorithm stores heart rate and heart rate variability data associated with arrhythmias in a second user and determines said presence of said arrhythmia in said first user based on said stored heart and heart rate variability data associated with arrhythmias in said second user.

* * * * *

(12) INTER PARTES REVIEW CERTIFICATE (3839th)

United States Patent
Gopalakrishnan et al.

(10) Number: US 10,159,415 K1
(45) Certificate Issued: Dec. 23, 2024

(54) METHODS AND SYSTEMS FOR ARRHYTHMIA TRACKING AND SCORING

(71) Applicants: Ravi Gopalakrishnan; Lev Korzinov; Fei Wang; Euan Thomson; Nupur Srivastava; Omar Dawood; Iman Abuzeid; David E. Albert

(72) Inventors: Ravi Gopalakrishnan; Lev Korzinov; Fei Wang; Euan Thomson; Nupur Srivastava; Omar Dawood; Iman Abuzeid; David E. Albert

(73) Assignee: ALIVECOR, INC.

Trial Number:

IPR2022-01562 filed Sep. 26, 2022

Inter Partes Review Certificate for:

Patent No.: 10,159,415
Issued: Dec. 25, 2018
Appl. No.: 15/393,077
Filed: Dec. 28, 2016

The results of IPR2022-01562 are reflected in this inter partes review certificate under 35 U.S.C. 318(b).

INTER PARTES REVIEW CERTIFICATE
U.S. Patent 10,159,415 K1
Trial No. IPR2022-01562
Certificate Issued Dec. 23, 2024

AS A RESULT OF THE INTER PARTES REVIEW PROCEEDING, IT HAS BEEN DETERMINED THAT:

Claims 10 and 20 are found patentable.

Claims 1-9 and 11-19 are cancelled.

\* \* \* \* \*